| (12) | United States Patent | (10) Patent No.: | US 9,237,762 B2 |
|---|---|---|---|
| | Larsson et al. | (45) Date of Patent: | Jan. 19, 2016 |

(54) AQUEOUS DISPERSION COMPRISING GALACTOLIPIDS AND METHOD FOR PRODUCTION THEREOF

(75) Inventors: Kare Larsson, Bjarred (SE); Magnus Harrod, Alingsas (SE)

(73) Assignee: SWEDISH OAT FIBER AB, Varobacka (SE)

( * ) Notice: Subject to any disclaimer, the term of this patent is extended or adjusted under 35 U.S.C. 154(b) by 59 days.

(21) Appl. No.: 13/699,663

(22) PCT Filed: May 24, 2011

(86) PCT No.: PCT/SE2011/050646
§ 371 (c)(1),
(2), (4) Date: Feb. 1, 2013

(87) PCT Pub. No.: WO2011/149416
PCT Pub. Date: Dec. 1, 2011

(65) Prior Publication Data
US 2013/0129801 A1 May 23, 2013

Related U.S. Application Data

(60) Provisional application No. 61/347,643, filed on May 24, 2010.

(30) Foreign Application Priority Data

May 24, 2010 (SE) ...................................... 1050515

(51) Int. Cl.
| *A23L 1/30* | (2006.01) |
| *A23D 7/005* | (2006.01) |
| *A61K 9/127* | (2006.01) |
| *A61K 36/899* | (2006.01) |
| *A61K 8/04* | (2006.01) |
| *A61K 8/06* | (2006.01) |
| *A61K 8/14* | (2006.01) |
| *A61K 8/92* | (2006.01) |
| *A61K 9/10* | (2006.01) |
| *A61K 9/107* | (2006.01) |
| *A61K 31/7028* | (2006.01) |
| *A61K 47/44* | (2006.01) |

(52) U.S. Cl.
CPC ............. *A23L 1/3006* (2013.01); *A23D 7/0053* (2013.01); *A23D 7/0056* (2013.01); *A61K 8/04* (2013.01); *A61K 8/062* (2013.01); *A61K 8/14* (2013.01); *A61K 8/92* (2013.01); *A61K 9/10* (2013.01); *A61K 9/107* (2013.01); *A61K 9/127* (2013.01); *A61K 9/1272* (2013.01); *A61K 9/1274* (2013.01); *A61K 9/1277* (2013.01); *A61K 31/7028* (2013.01); *A61K 36/899* (2013.01); *A61K 47/44* (2013.01)

(58) Field of Classification Search
CPC ........... A61K 8/04; A61K 8/062; A61K 8/14; A61K 9/10; A61K 9/107; A61K 9/1274; A61K 9/1277

See application file for complete search history.

(56) References Cited

U.S. PATENT DOCUMENTS

| 4,598,089 A | 7/1986 | Hadvary et al. | |
| 5,688,528 A | 11/1997 | Carlsson et al. | |
| 5,716,639 A * | 2/1998 | Carlsson ............... | A23D 7/0053 424/450 |
| 6,022,561 A * | 2/2000 | Carlsson ............... | A23D 7/0053 424/401 |
| 2007/0154539 A1 | 7/2007 | Fountain | |

FOREIGN PATENT DOCUMENTS

| CN | 101632637 A | 1/2010 |
| EP | 1 297 48 A1 | 1/1985 |
| JP | 2007204368 A | 8/2007 |
| WO | 87/03198 A1 | 6/1987 |
| WO | 95/20944 A1 | 8/1995 |
| WO | 97/13500 A2 | 4/1997 |
| WO | 99/02041 A1 | 1/1999 |
| WO | 9955308 A1 | 11/1999 |
| WO | 00/40247 A1 | 7/2000 |
| WO | 0202716 A2 | 1/2002 |
| WO | 02068561 A2 | 9/2002 |
| WO | 02068562 A2 | 9/2002 |

(Continued)

OTHER PUBLICATIONS

Bottier, C.; Gean, J.; Artzner, F.; Desbat, B.; Pezolet, M.; Renault, A.; Marion, D.; Vie, V. "Galactosyl headgroup interactions control the molecular packing of wheat lipids in Langmuir films and in hydrated liquid-crystalline mesophases" Biochimica et Biophysica Acta 2007, 1768, 1526-1540.*

(Continued)

*Primary Examiner* — Sean Basquill
*Assistant Examiner* — Andrew S Rosenthal
(74) *Attorney, Agent, or Firm* — Young & Thompson

(57) ABSTRACT

A method for preparing a dispersion of polar lipids in an ethanol-water mixture, the polar lipids including galactolipids. An oil containing polar lipids including galactolipids is diluted using a first ethanol-water mixture having an ethanol concentration close to the critical polarity, wherein upon dilution the polar lipids form a lamellar liquid-crystalline phase, without first forming a hexagonal HII-phase. The invention also refers to an oil obtained by evaporating ethanol and water from the dispersion. The invention further refers to aqueous colloidal dispersions of polar lipids including galactolipids, to an oil containing polar lipids including galactolipids and to pharmaceutical, cosmetic and food compositions including such dispersions and/or oil.

41 Claims, 15 Drawing Sheets

(56) References Cited

FOREIGN PATENT DOCUMENTS

Figure 1:
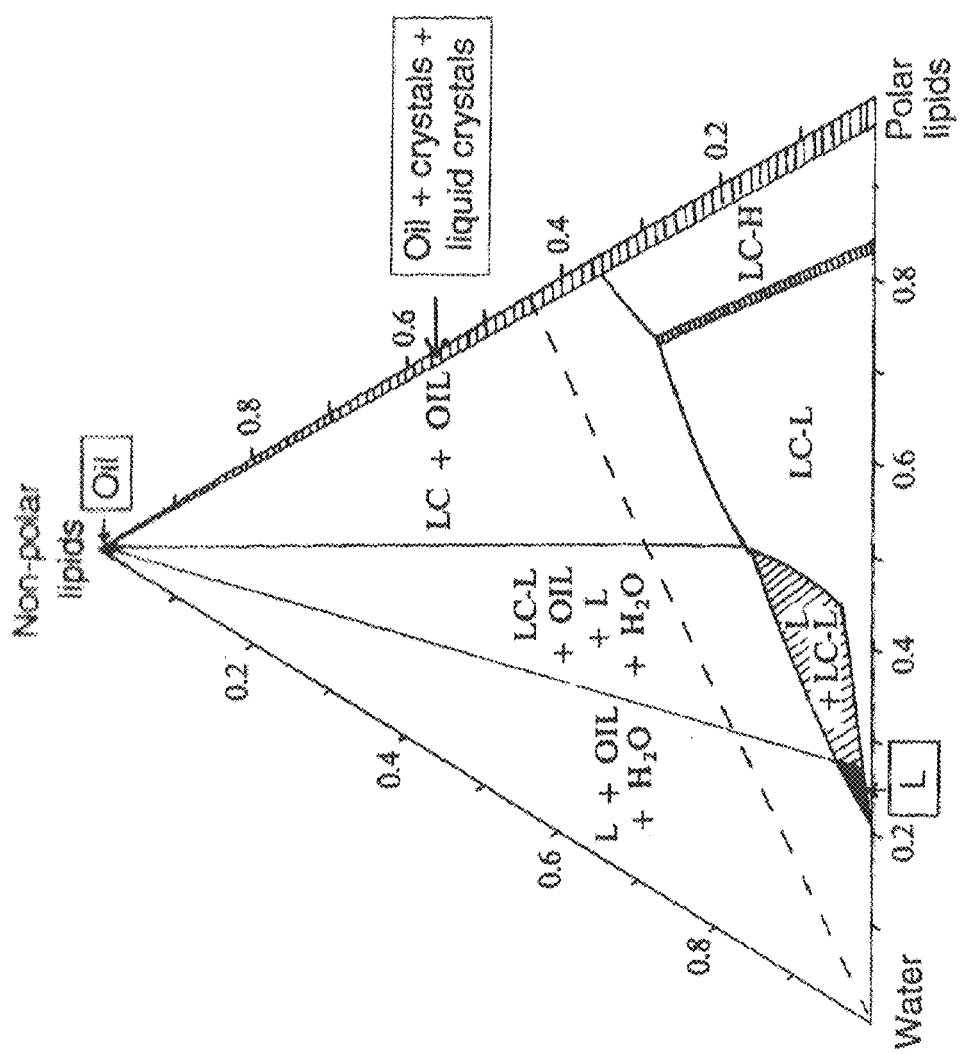

| WO | 03/018529 | A1 | 3/2003 | |
|---|---|---|---|---|
| WO | 2006/053647 | A1 | 5/2006 | |
| WO | 2006/117069 | A1 | 11/2006 | |
| WO | 2006/132586 | A1 | 12/2006 | |
| WO | 2007026151 | A1 | 3/2007 | |
| WO | WO 2007026151 | A1 * | 3/2007 | |
| WO | 2007/075142 | A1 | 7/2007 | |
| WO | 2009/068651 | A1 | 6/2009 | |
| WO | WO 2009068651 | A1 * | 6/2009 | ............... A23C 9/13 |
| WO | 2009/31436 | A1 | 10/2009 | |

OTHER PUBLICATIONS

Pons, M.; Foradada, M.; Estelrich, J. "Liposomes obtained by the ethanol injection method" International Journal of Pharmaceutics 1993, 95, 51-56.*

Garg, G.; Saraf, S.; Saraf, S. "Cubosomes: An Overview" Biol. Pharm. Bull. 2007, 30(2) 350-353.*

Bottier et al., "Galactosyl headgroup interactions control the molecular packing of wheat lipids in Langmuir films and in hydrated liquid-crystalline mesophases", Biochimica et Biophysica Acta 1768 (2007), 1526-1540, abstract, p. 1536, col. 2, paragraph [0043]-paragraph [0044], Cited in ISR.

International Search Report, dated Sep. 22, 2011, from corresponding PCT application.

Fan et al., "Preparation of salidroside nano-liposomes by ethanol injection method and in vitro release study", Eur. Food Res. Technol., 2008, vol. 227, pp. 167-174.

Li et al., "Preparation and stability of digalactosyl diglyceride as emulsifier for sub-microemulsion", School of Pharmacy, 2009, vol. 34, pp. 2172-2176.

Pons et al., "Liposomes obtained by the ethanol injection method", International Journal of Pharmaceutics, 1993, vol. 95, pp. 51-56.

* cited by examiner

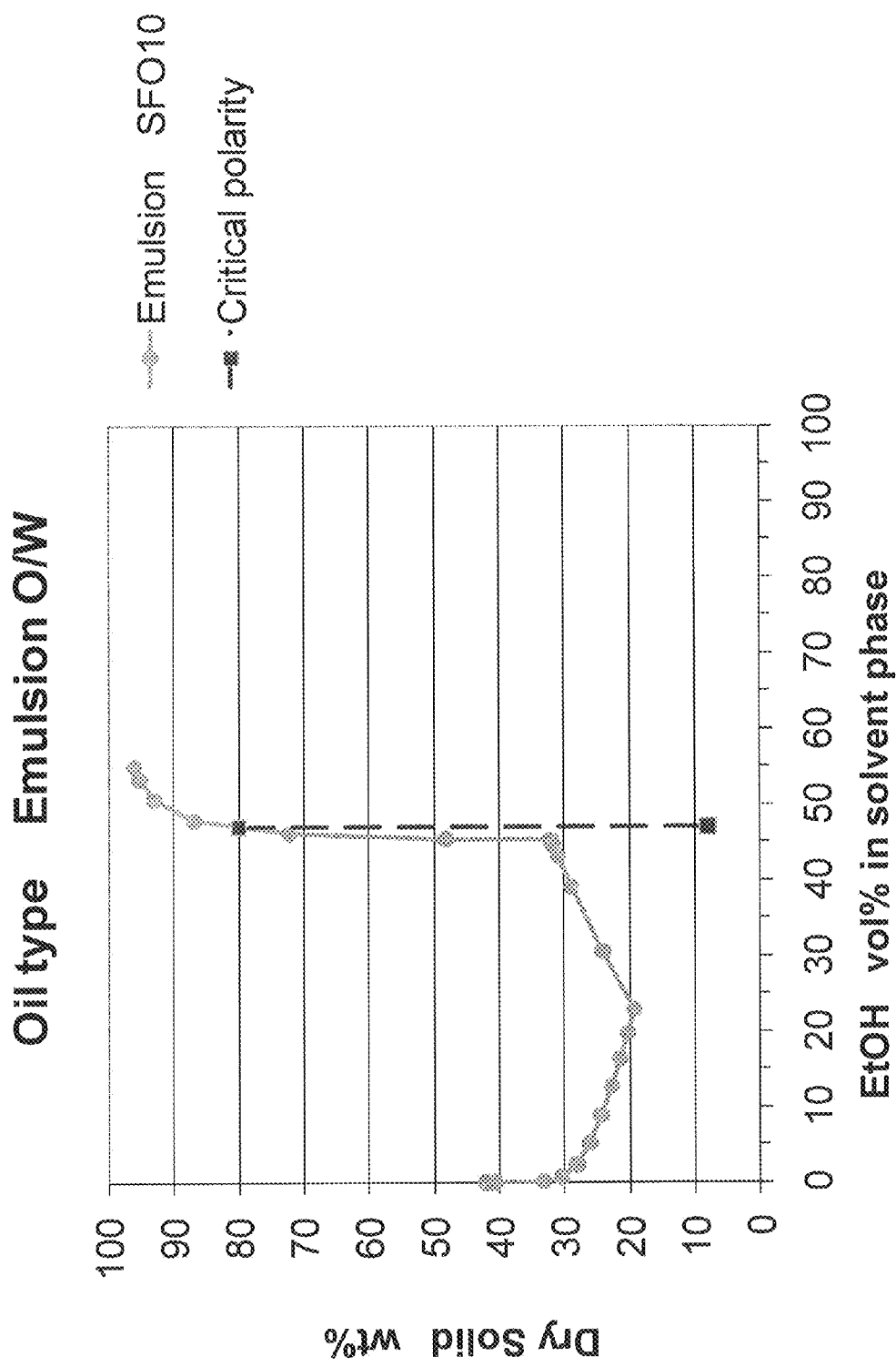

AQUEOUS DISPERSION COMPRISING GALACTOLIPIDS AND METHOD FOR PRODUCTION THEREOF

1. TECHNICAL FIELD

This invention refers to a method for preparing a dispersion of polar lipids in an ethanol-water mixture, said polar lipids comprising galactolipids. The invention also refers to an oil obtained by evaporating ethanol and water from the dispersion. The invention further refers to aqueous colloidal dispersions of polar lipids comprising galactolipids, to an oil containing polar lipids comprising galactolipids and to pharmaceutical, cosmetic and food compositions comprising such dispersions and/or oil.

2. BACKGROUND OF THE INVENTION 2.1. Lipid Phase Behaviour and Aqueous Lipid Particle Dispersions Lipids of vegetable origin consist of polar and non-polar components. The non-polar lipids are of great importance in foods, providing raw materials for fats or oils. The polar lipids are mainly used in order to achieve special functional properties, such as emulsification. The term polar lipid is used in this context based on the interaction with water; thus lipids forming aqueous phases are termed polar, whereas a lipid sample which do not form aqueous phases are termed non-polar. Polar lipids of vegetable origin are obtained at the so-called degumming step in the refining process of oil crops, such as soy bean oil. These lipids are dominated by phospholipids. Another source of polar lipids is cereals, containing a mixture of phospholipids and galactolipids. In this invention we have started from ethanol-water solutions of mixtures of galactolipids and phospholipids, with focus on ethanol extracts of oats, in which the polar lipids have been enriched by fractionation. At a certain concentration of the lipids in ethanol-water mixtures of a particular composition, a fluid was formed containing aggregates of a liquid-crystalline state which as far as we know never earlier has been reported in lipids. The molecular organization in this fluid and transformations at water dilution/ethanol evaporation is utilized in our invention.

Dispersions of the lamellar liquid-crystalline phase in an aqueous environment, which were termed liposomes, were first described in the 1960s. These particles consist of spherically concentric lipid bilayers alternating with water layers. They are formed from the lamellar liquid crystalline-phase, the L-alpha phase, by mechanical dispersion in excess of water. Thus a prerequisite is that the L-alpha phase can coexist in equilibrium with a water phase. The liposomes prepared from the L-alpha phase consist of several concentric bilayers, and are also termed multilamellar vesicles. There are also specific methods described in the literature for preparations resulting in unilamellar vesicles, which have been applied particularly in drug delivery. This invention describes a new method to prepare monodisperse aqueous dispersions of vesicles of galactolipids and phospholipids of very small size, and the use of such particles.

There is an extensive literature on manufacture and use of liposomes. The dominating lipids used are phospholipids and the most common applications involve delivery of biologically active components for pharmaceutical and food use.

Liposomes are usually formed by mechanical homogenization of the lamellar liquid-crystalline phase in excess of water, including ultrasonification and use of valve homogenizers. Commonly used reported methods in the literature involve the dry film method and the ethanol injection method. In order to obtain liposomes or vesicles of uniform size, molecular sieve methods have been used.

There are also other liquid-crystalline phases in lipid-water systems. The most important ones are beside the earlier mentioned L-alpha phase, the inverse hexagonal liquid-crystalline phase, also termed HII-phase, and cubic phases. These can also form aqueous dispersions. The introduction of the cryo-TEM method has allowed a detailed structural description of both inverse cubic and hexagonal particles in water (Langmuir 12 (1996) 4611-4613 and 13 (1997) 6964-6971. J. Gustaysson, H. Ljusberg-Wahren, M. Almgren, K. Larsson respectively). In the text below the lamellar liquid-crystalline phases is termed L-alpha phase, and the inverse hexagonal liquid-crystalline phase is termed HII-phase.

During the development of a preparation process of vesicle dispersions of polar lipids prepared from oats we realized that the same process could be applied in order to prepare uniform particle dispersions of oil-in-water and furthermore by introducing monoglycerides into mixtures of phospholipids and galactolipids uniform particle dispersions of cubic-phases could also be efficiently prepared.

We have developed a step-wise ethanol/water dilution process in order to prepare colloidal dispersions of polar lipids and it is described in detail here in the case of oat lipid fractions. This process was introduced mainly to avoid formation of the HII-phase at direct water exposure. This method was found to produce unilamellar vesicles in a smaller size range than earlier described. Prior art process required extremely pure polar lipid fractions as starting material. Our new process enables use of less purified staring material and at the same time accepts a higher load of active ingredient in delivery systems, while maintaining or improving the functional properties of the dispersion.

2.1.1 Prior Art and their Relations to Our Invention

As we use ethanol solutions we will consider here prior art for lipid particle preparation involving ethanol. A method based on ethanol solution droplets exposed to a water phase that has become important for liposome preparation was introduced long time ago (S. Batzri and E. Korn: Biochim. Biophys. Acta 298 (1973) 1015-1019). They injected an ethanol solution of phospholipids into the water phase. Large-scale production using this method has also been reported, cf. (R. Naeff: Adv. Drug Delivery Rev. 18 (1996) 343-347), including preparation of tuneable particle size distributions controlled by needle diameter in combination with hydrodynamic pressure (P. Prahan, J. Guan, P. G. Wang, L. J. Lee, R. J. Lee: Anticancer Res. 28 (2008) 943-947).

The use of ethanol for preparation of cubic particles was introduced by Spicer and co-workers and is further discussed below in connection with such particles.

These applications of direct water-dilution of ethanol solutions of the lipids are fundamentally different from our ethanol-water dilution process to produce particle dispersions. The earlier described prior art methods cannot be applied to our galactolipid and phospholipid systems as gel phases with the hexagonal HII-phase will be formed irreversibly.

In our case the ethanol-water dilution of the ethanol-lipid mixture must be carefully controlled so as to avoid formation of the hexagonal HII-phase. At ethanol concentrations higher than a critical ethanol concentration, the HII-phase cannot form. By dilution of an oil containing polar lipids, using an ethanol solution with a concentration close to the critical concentration, it is possible to separate the lamellar phase directly without formation of any HII-phase.

The prior art processes require extremely pure polar lipid fractions as starting material. Our new process enables use of less purified staring material and at the same time the particles can carry a higher load of active ingredients in delivery applications, while the functional properties of the dispersion are maintained or improved.

The interaction of cereal lipids with water has been analysed in detail in the case of wheat lipids, which resulted in the ternary phase diagram shown in FIG. 1. Similar phase equilibria occur also for oat lipids as shown below. The phase diagram shows phase equilibria of wheat lipids and water at room temperature. The polar and non-polar wheat lipid components were first separated and then reconstituted in different proportions before equilibration with water. Two liquid-crystalline phases exist—the lamellar (LC-L) and the inverse hexagonal (LC-H) and one liquid phase (L) as identified by X-ray diffraction. The broken line shows the composition polar/non-polar lipids in the wheat endosperm (after Larsson et al. 2006 *Lipids: Structure, Physical properties and Functionality*, The Oily Press)

The phase equilibria and physical structures of lipid extracts from oats are in general agreement with the wheat lipid system (G. Jayasingha, K. Larsson, Y. Miezis and B. Sivik. J. Dispersion Sci. Techn. 12 (1991) 443).

From FIG. 1, it can be seen that at a polar lipid concentration above 65 lipid % and addition of water the hexagonal phase HII is formed. The hexagonal phase creates a gel and this gel is extremely viscous and impossible to disperse into small particles.

However, the starting material in this invention contains ethanol. Thus a fourth dimension is introduced. In oat lipids with ethanol the formation of HII-gel occurs when the lipids are diluted in water, see Example 1. Once formed it takes very long time to dissolve the HII-gel. At room temperature the time scale is years.

At direct dilution of the oat lipid fractions of this invention, the HII-phase is always formed before the L-alpha phase, see Example 1, and therefore the prior art methods to produce liposomes in phospholipid systems cannot be applied. When the HII-phase is formed in phase diagrams of phospholipids, there appears to be an existence region of the L-alpha phase at lower temperature, where water dilution towards liposomes can take place.

By diluting the lipids with an ethanol-water solution according to a carefully designed protocol, defined in this invention, formation of the HII-particles can be avoided. This procedure is a prerequisite for the formation of the very small particles presented in this invention. In this way we can produce very small particles using lipid-mixtures of wide composition variations and with high concentrations, and this allows us to load more active components in the particles compared to prior art. The lipids used here form the liquid crystalline phase at and above room temperature so processing can be done at room temperature. The carefully designed ethanol-water dilution protocol also enables production of polar lipid fractions free from ethanol in a reproducible way without HII-particles. These polar lipid fractions have a very high and stable capacity to make oil-in-water emulsions.

There are only a few reported applications of cereal lipids and galactolipids which are discussed in detail below:
1. WO9520944 (U.S. Pat. No. 6,022,561) describes "bilayer preparations" which are prepared from chromatographically purified cereal extracts resulting in a polar lipid concentration of 100% and a concentration of DGDG above 67% (see their table 1) for producing carrier particles for active ingredients, in the form of either a gel or liposomes which are shown to be multilamellar. These very pure polar lipids could be mixed with water without formation of HII. After ultrasonication the average particle size of the vesicles was 144 nm.

The small unilamellar vesicles we obtain have average particle size below 100 nm. In addition the cubosomes we describe cannot be formed by their technology. Note also that we achieve much smaller particles using polar lipids with a much lower purity.

2. WO 2009/131436A1 describes a yoghurt product with an oil-in-water emulsion for satiety enhancement, and in the formulation of the complex mixture they use galactolipids as emulsifier (claim 3), and also oat lipids are mentioned (claim 4). The particles size for the oil-in-water (O/W) stabilized with an additional stabilizer, was such that at least 75% of the particles should be smaller than 1000 nm. Thus, their process will never obtain the O/W emulsions we describe.

3. WO 2009/068651 A1 describes an O/W emulsion for lowering cholesterol by phytosterols as a component in all claims. Galactolipids are used as emulsifier. Particle sizes are not given.

4. Li X. et al, Preparation and stability of DGDG as emulsifier for sug-microemulsions, Zhongguo zhongyao zazhi 2009, 34(17) 1272-1276 (AN2009:1571859) describes that digalactosyl diglycerides are used to make a submicro-emulsion of "bay oil" as a model drug. The particle size after high pressure homogenisation was 168 nm. Thus the particles are significant larger than the particles from our process.

2.1.2 Conclusion on Lipid Particles

Within a wide range of proportions between galactolipids and other components of oat or other cereal lipids, the formation of an HII-phase is a serious complication for formation of uniform vesicle dispersions. This invention provides a solution to this problem.

During the development of the preparation process focused towards vesicle dispersions in water of oat lipids it was realized that this process also can be applied to preparation of polar lipid fractions free from ethanol and HII crystals, oil-in-water emulsions and furthermore cubic liquid-crystalline particles in water can be prepared when monoglycerides are introduced into the cereal lipid mixture.

2.2 Appetite Regulation

Obesity is a big and increasing problem in the western society. It has been estimated that $45 billion of US healthcare costs, or 8% per annum of total healthcare spend, is a direct result of obesity. Traditional approaches to long term weight management such as diet and exercise have proved ineffective alone to control the spread of obesity. Today, more than ever, there is a considerable interest in developing safe, effective methods for treatment of obesity.

Pharmacological approaches to the treatment of obesity have focused on either developing drugs that increase energy expenditure or drugs that reduce energy intake. One approach to the reduction of energy intake is to reduce the body's ability to digest and adsorb food, in particular fat. The key enzyme involved in digestion of fat is pancreatic lipase that is secreted by pancreas into the gut lumen.

The lipase inhibitor lipstatin has formed the basis of the anti-obesity drug, orlistat. Orlistat and its use in inhibiting pancreatic lipase and treating hyperlipaemia and obesity is disclosed in EP129748 (Hoffmann-la Roche, 1984). The use of orlistat (Xenical) as a drug against obesity is well established (Sjöström L. et al., Lancet 352: 167-172, 1998). The proposed mechanism is that less fat will be absorbed and therefore you will reduce your energy intake and consequently reduce your weight. The drawback with this lipase inhibitor is that it inhibits all types of lipases and produces steatorrhea due to strongly impaired fat digestion. It is therefore of outmost importance to develop a natural compound that retards fat digestion in a milder way without causing steatorrhea as side effect.

Cetilistat is another lipase inhibitor disclosed in WO00/40247, (Alizyme Therapeutics, 2000) with similar working mechanism, but with less side effects than orlistat (Kopelman P. et al., Int J Obes 2006; 31: 465-71).

Energy balance is a homeostatic system. Although malfunctions of this system can cause obesity, the relatively recent increase in the incidence of obesity is not thought to be the result of specific defects, but of a regulatory system unable to cope with the current context of cheap, high-energy foodstuffs, mechanized transport and non-manual labour. Commandeering elements of this regulatory system might provide the best opportunity for us to combat obesity (Murphy K. Bloom S., Nature 2006; 444: 854-859).

The "ileal brake" is a feedback mechanism activated by nutrients in the intestine, especially fat, with marked effects on satiety. Small amounts of fat are able to induce satiety and influence food intake (Welch I., et al. Gastroenterology 1985; 89: 1293-1297; Welch I., et al. Gut 1988; 29: 306-311; Greenberg D. and Smith, G. P., Psychosomatic medicine 1996; 58: 559-569; Maljaars P W J., et al, Int. J. Obesity 2008; 32: 1633-1639).

WO87/03198 refers to an enteric preparation in the form of a capsule or tablet containing a fat as the active substance that should be released in the intestine. This preparation utilizes the ileal brake mechanism.

WO99/02041 and WO2007/075142 disclose the use of emulsions based on fractionated palm oil and fractionated oat oil to bring fat far down in the intestine. This product (Olibra, DSM) is investigated in several studies (Burns A. A. et al., Int. J Obesity 2000; 24:1419-1425; Burns A. A. et al., Int. J Obesity 2001; 25:1487-1496; Burns A. A. et al., Eur J Clin Nutr 2002; 56:368-377; Logan C:M: et al., Eur J Clin Nutr 2006; 60:1081-1091; Diepvens K. et al., Int. J Obesity 2007; 31:942-949; Diepvens K. et al., Physiol Behav 2008; 95:114-117). A statistical significant effect is demonstrated in some cases. However, it is questionable if the effect can be considered as clinical.

Emulsions based on palm oil and proteins from partially denatured egg white, as disclosed in WO2006/053647, Unilever, and rapeseed oil or hydrogenated rapeseed oil together with milk protein and monoglycerides, as disclosed in WO2006/117069, Unilever, are also used to bring fat far down in intestine.

In WO2006/132586 (Albertsson) whole biological membranes or the hydrophobic peptides of biological membranes are used for the reduction of lipolytic activity and/or retard fat digestion, suppress appetite, body weight and/or lower blood lipids.

WO97/13500 refers to liposome formulations having incorporated therein an amount of a 5-β steroid effective to treat obesity, diabetes or hydrocortocoidism.

WO03/018529 refers to fatty-acid monoesters of an estrogen and a fatty acid for use in treatment of obesity and overweight. In a preferred pharmaceutical or cosmetic composition for intravenous injection the monoester is incorporated in a lipidic suspension prepared from liposomes.

JP2007204368 refers to a silk peptide as active ingredient useful in treatment of obesity, wherein the silk peptide is incorporated into a liposome.

Even if these products provide effective for treating obesity, there remains a need to provide improved methods for use in control and treatment of obesity and obesity-related diseases.

2.2.1 Proposed Mechanism and Initial Results in this Invention

Our process enable production of very small (smaller than 100 nm), uniform particles of unilamellar vesicle type. The mechanism for enhancement of satiety is assumed to be the following: These lipid particles, with extremely large surface area and very rich in galactolipids, interact with the lipases in the intestine and the reduced enzyme activity increases the concentration of lipids in the end of intestine. This activates the "ileal break mechanism" for satiety. We can control the enzyme activity and achieve sufficient satiety without any negative side effects. A particular advantage is that the lipids we use are components of a common food material, which eliminates any safety risks.

As a first step in proving this invention on satiety, a clinical evaluation under controlled conditions has been done. A morning meal containing a particle dispersion of oat lipid vesicles gave significant effects on GLP-1, which is a hormone in the blood and used as an indicator on satiety. This study is described in Example 7 below. An extended clinical study is now performed.

2.3. Encapsulation or Solubilization for Increasing Bioavailability of Valuable Nutrients in Foods and Feed Within the field of formulation technology, various methods have been developed in order to solubilize encapsulate, and deliver biologically active materials. Our invention provides new application possibilities of nutrients or other important food components, such as antioxidants and aroma substances. These processes involve solubilization or encapsulation of the actual component in our particle carrier systems. In this way increased bioavailibility can be obtained The most advanced applications in this field are found in drug delivery, which involves controlled administration of a pharmaceutical active material in order to achieve a therapeutic effect. An authority in this field Robert S, Lang stated that the current needs in this field are to reduce toxicity, to increase absorption and to improve release profile (C. M. Henry, Chem. & Engineering News 80 (2002) 39-47). Lipids are frequently applied, and the introduction of liposomes has proved to reduce toxicity in an application involving doxorubicin (the product Doxil is used in cancer therapy). A drug incorporated into a liposome is released by diffusion or released into the targeted cells by endocytosis. Some advanced recent studies are focused on drug targeting by attached ligands on the surface of the liposomes which bind to specific cell surface receptors. The general properties of lipid particles described in the present invention offer similar application possibilities as liposomes. They can be expected to be superior with regard to drug load and mechanical properties of the particles.

There are obviously many common features in gastrointestinal drug delivery and delivery of special food components. The present knowledge of delivery in food systems have recently been described in an excellent review by Sagalowicz and Leser (Delivery systems for liquid food products, *Current Opinion in Colloid & Interface Science* (2009), doi: 10.1016/j.cocis.2009.12.003). Sensitive molecules can be protected against degradation (such as oxidation during storage of the actual food product) and the most important aspect is that the bioavailability of important nutrients can be improved.

2.3.1 Conclusion Encapsulation and Solubilisation

The present invention provides new possibilities in this field. One application enables production of very small (smaller than 100 nm), uniform particles of self assembly type. Only limited mixing energy is required in the process. Also the preparation of particles of cubic lipid liquid-crystalline phases can be useful in this field. A wide range of molecules can be added into the particles, both hydrophilic and lipophilic molecules. A particular advantage is that the lipids we use are components of a common food material, which eliminates safety risks.

2.4 Method to Utilize the Full Emulsifying Capacity of Oils Containing Galactolipids in Emulsions Already in the 1960s Stig Friberg demonstrated the important role of the lamellar liquid-crystalline phase in emulsion formation and stability. Now it is generally accepted that food emulsions stabilized by polar lipid must provide the lamellar liquid-crystalline phase during the emulsification process (cf. K. Larsson and Stig Friberg: Food Emulsion second ed. Marcel Dekker Inc., New York 1960).

The mechanism behind the emulsification is that the non-polar oil separates simultaneously as the lamellar liquid-crystalline phase is formed and the lamellar phase will then tend to coat the oil droplets spontaneously in order to reduce the surface energy of the dispersion. Such emulsions are kinetically stable at a solid content above about 40 vol %.

This also means that if the HII-phase is formed before the lamellar phase, there is a serious complication hindering the application of standard mechanical emulsification processes. The starting lipid material we use comprises galactolipids as a polar lipid component. Galactolipids may form HII-particles. Using traditional emulsifying methods on oils containing galactolipids may fail or become difficult to reproduce because formation of HII-particles. Large amounts of energy are required to emulsify oil in water. It is difficult to get the particles small enough, to get a sufficient narrow particle size distribution and the variation between batches are very high.

By using the methods presented in this invention we can circumvent the ranges where HII particles are formed and the energy consumption is reduced, the particle size is reduced, the particle size distribution is narrower and the variation between batches is reduced.

2.5 Removal of Ethanol from Oils Containing Galactolipids without Forming HII-Particles When ethanol is removed from oil fractions containing galactolipids and ethanol there is a risk that HII-particles are formed. Once formed it may take years before the HII-particles are dissolved. This means that oils containing HII-particles lose their emulsifying properties.

Therefore there is a great need to find methods to remove ethanol from oils containing galactolipids without forming HII-particles.

By using the methods presented in this invention we can; circumvent the ranges where HII particles are formed during removal of ethanol from oils containing galactolipids; reduce energy consumption, the particle size, the particle size distribution and reduce the variation in product quality between batches in downstream processes.

3 SUMMARY OF THE INVENTION

The invention refers to a method for preparing a dispersion of polar lipids in an ethanol-water mixture, said polar lipids comprising galactolipids, characterized in diluting an oil containing polar lipids comprising galactolipids using a first ethanol-water mixture having an ethanol concentration close to the critical polarity, wherein upon dilution said polar lipids form a lamellar liquid-crystalline phase, without first forming a hexagonal HII-phase.

Said first ethanol-water mixture may have an ethanol concentration calculated as volume % based on the total amount of ethanol and water, which is in the range from 15 volume % units, preferably from 10 volume % units and more preferably from 5 volume % units, below the critical polarity of the ethanol-water mixture with respect to said oil to 15 volume % units, preferably to 10 volume % units and more preferably to 5 volume %, above said critical polarity.

The critical polarity of said first ethanol-water mixture may be in the range 25-75, preferably 30-70, more preferably 35-65, even more preferably 40-60 and most preferably in the range 45-55 volume % ethanol in the solvent phase.

Dilution of said dispersion may be proceeded with said first ethanol-water mixture and/or a second ethanol-water mixture and/or with water until a colloidal dispersion of said polar lipids is obtained, wherein said polar lipids form colloidal particles in the form of liposomes, cubic particles and/or oil droplets coated by lamellar liquid-crystalline phase.

The relationship in volume % between ethanol and water in the second ethanol-water mixture used for diluting the polar lipids forming a lamellar liquid crystalline phase in said first ethanol-water mixture may be different than in said first ethanol-water mixture, such that the second ethanol-water mixture may contain a higher proportion of water than the first polar solvent mixture.

Following the proceeded dilution of said dispersion comprising said polar lipids in a lamellar liquid-crystalline phase, a colloidal dispersion of liposomes may be obtained.

Said liposomes may have a mean diameter which is less than 100 nm.

At least 80% of the liposomes may have a diameter of less than 200 nm.

Said liposomes may be in the form of unilamellar vesicles having one bilayer of polar lipids.

Said oil may contain at least 25 weight % monoglycerides of oleic and/or linolic acid as calculated on the total amount of lipids in said oil, wherein following the proceeded dilution of said dispersion comprising said polar lipids a colloidal dispersion of cubosomes may be formed.

Ethanol may be evaporated from the dispersion to provide an aqueous dispersion containing less than 10 weight %, preferably less than 5 weight % and more preferably less than 1 weight % ethanol.

The polar lipids may be derived from plants, animals or microbiological species.

The polar lipids may be derived from cereal grains or leaves.

The polar lipids may be derived from oat.

Said polar lipids may also comprise phospholipids.

Said oil may contain between 30-95, preferably between 30-90 lipid % non-polar lipids and that said dispersion contains at least 30 weight %, preferably at least 40 weight % and more preferably at least 50 weight % total lipids, resulting in an oil-in-water emulsion in which the non-polar lipids form oil droplets that are coated by a lamellar liquid-crystalline phase of said polar lipids.

Ethanol and water may be evaporated from said dispersion to provide an oil containing less than 1 wt % ethanol.

Said oil may be derived from oat.

The invention further refers to an aqueous colloidal dispersion of polar lipids, said polar lipids comprising galactolipids, wherein said polar lipids comprising galactolipids form nano size liposomes having a mean diameter which is less than 100 nm At least 80% of the liposomes may have a diameter of less than 200 nm.

The liposomes may have a mean diameter which is not more than 80 nm, preferably not more than 60 nm.

At least 80%, preferably at least 90% and more preferably at least 99% of the nano size liposomes may have a diameter of less than 100 nm.

The liposomes may have a mean diameter in the range 30-60 nm, preferably in the range 40-50 nm.

The liposomes may be unilamellar vesicles having one bilayer of polar lipids.

At least 25 weight % may be monoglycerides of oleic and/or linolic acid as calculated on the total amount of lipids, said polar lipids comprising galactolipids, wherein the polar lipids comprising galactolipids and the monoglycerides form colloidal cubosomes.

The polar lipids may be derived from plants, animals or microbiological species.

The polar lipids may be derived from cereal grains or leaves.

The polar lipids may be derived from oat.

The polar lipids may also comprise phospholipids.

The liposomes and/or cubosomes may contain at least 50 lipid % of polar lipids, preferably at least 60 lipid % and more preferably at least 75 lipid % of polar lipids, the rest of the lipids being non-polar lipids, wherein lipid % refers to the weight % of polar lipids calculated on the total amount of lipids.

The liposomes may contain at least 2 lipid %, preferably at least 5 lipid % and preferably at least 10 lipid % of non-polar lipids, the rest of the lipids being polar lipids, wherein lipid % refers to the weight % of non-polar lipids calculated on the total amount of lipids.

The dispersion may have a dry solid content of less than 20 weight %.

The invention further refers to an aqueous colloidal dispersion in the form of an oil-in-water emulsion of polar lipids comprising galactolipids and non-polar lipids, wherein the non-polar lipids form oil droplets that are coated by a lamellar liquid-crystalline phase of said polar lipids.

The invention also refers to an aqueous colloidal dispersion obtainable by a method defined above.

The invention also refers to an oil containing polar lipids comprising galactolipids, wherein said oil contains less than 1 wt % ethanol and less than 3 wt % sugar, preferably less than 2 wt % sugar and more than 25 wt % polar lipids, preferably more than 30 wt % polar lipids and said oil is also characterized in forming less hexagonal phase than lamellar liquid-crystalline phase during a following water swelling process which results in a spontaneous emulsification.

Said oil may be derived from oat.

The invention further refers to an aqueous colloidal dispersion as defined above or obtainable according to the method as defined above for use as a medicament.

The invention further refers to an aqueous colloidal dispersion and/or oil as defined above or obtainable according to the method as defined above for treatment of obesity, increased blood lipid levels, diabetes type II and/or autoimmune diseases including rheumatoid arthritis and multiple sclerosis.

The invention further refers to the use of an aqueous colloidal dispersion and/or oil as defined above or obtainable according to the method as defined above for the manufacture of a medicament for the treatment of obesity, increased blood lipid levels, diabetes type II and/or autoimmune diseases including rheumatoid arthritis and multiple sclerosis.

The invention further refers to a pharmaceutical formulation comprising an aqueous colloidal dispersion and/or oil as defined above or obtainable according to the method as defined above optionally in admixture with a pharmaceutically acceptable adjuvant, diluent or carrier.

The dispersion and/or oil may act as an active ingredient or it may act as a carrier for release of an active ingredient.

The invention further refers to a cosmetic composition comprising an aqueous colloidal dispersion and/or oil as defined above or obtainable according to the method as defined above.

The invention further refers to a food composition or food supplement composition comprising an aqueous colloidal dispersion and/or oil as defined above or obtainable according to the method as defined above.

The food composition or food supplement composition may be margarine, oil, cream, milk, yoghurt, cheese, flour, juice, shot or soft drink.

The invention further refers to an animal feed composition comprising an aqueous colloidal dispersion and/or oil as defined above or obtainable according to the method as defined above.

The invention also refers to an article comprising an aqueous colloidal dispersion and or an oil as defined above or obtainable according to the method as defined above.

The invention further refers to a method of treating and/or preventing obesity, reducing blood lipid levels, diabetes type II and/or autoimmune diseases comprising the administration of a therapeutically effective amount of an aqueous colloidal dispersion and/or oil as defined above or obtainable according to the method as defined above to a mammal in need thereof.

4. DEFINITIONS

Stem Solutions
   T2, T7, HL17 and SFO10 are stem solutions, see Table 1
   PL0126 is an oat oil of T2-type and polar lipids=65 lipid %.
   PL13 is an oat oil of T7-type and polar lipids=85 lipid %
   HL17 is an oat oil of T2-type and polar lipids=40 lipid %
   SFO10 is sunflower oil and T2 mixed to polar lipids=10 lipid %
Oat Lipid Fraction Vesicle Dispersion
   T3 and T4, vesicle dispersions produced from T2 and T7, respectively
Colloidal Dispersions
   Colloidal dispersions are homogenous aqueous phases containing particles in the size range 1-1000 nm.
Liquid-Crystalline Lipid-Water Phases
   L-alpha—lamellar
   HII—inverse hexagonal
   Cubosomer
Thermotropic Liquid-Crystalline Phase
   Batonnet
Liposomes
   dispersion of an L-alpha phase
Unilamellar Liposomes=Vesicles
   dispersion of an L-alpha phase consisting of only one bilayer
Liquid Solvent Phases
   Lw=liquid phase starting in the water corner of a phase diagram ethanol/lipid/water
   Le=liquid phase starting in the ethanol corner of a phase diagram ethanol/lipid/water
Critical Polarity
   Critical polarity defines the concentration of ethanol and water of the solvent system when a solvent-in-oil emulsion is transformed into an oil-in-solvent emulsion and this critical polarity can be detected by viscosity or microscopy. When it is detected by viscosity, the viscosity starts to increase rapidly when increasing the polarity from the critical polarity. When it is detected using a polarized light microscope, the liposomes become much smaller when the polarity is increased from the critical polarity. When it is detected using a phase contrast light microscope, the size of the particles starts to decrease very fast when the polarity is increased from the critical polarity. The critical polarity is in the range 25-75 vol %, preferably 30-70 vol %, more preferably 35-65 vol %, even more preferably 40-60 vol % and most preferably 45-55 vol % ethanol in the solvent phase, wherein the solvent phase is as defined below.

To measure the critical polarity; the dry solid of the system should be in the range 10-80 wt %, more preferably 15-70 wt %, mostly preferred 20-65 wt %; and the ethanol concentration in the solvent phase should cover the critical polarity.

Example 2 describes a method to determine the critical polarity.

Close to Critical Polarity

Close to critical polarity means that the ethanol concentration in the first ethanol-water mixture should be in the range ±15 vol % from the critical polarity, more preferably in the range ±10 vol % from the critical polarity and most preferably in the range ±5 vol % from the critical polarity.

Oil

An oil is a liquid lipid phase containing non-polar lipids, polar lipids and ethanol, and it can also contain small amounts of water and sugar.

Solvent Phase

Solvent phase is a simplified calculated phase containing all ethanol and water in the system, without consideration of different concentration in different true phases EtOH vol % in Solvent Phase EtOH vol % in solvent phase is the calculated ethanol concentration in the solvent phase of the mixture used without consideration of different concentration in different phases.

E40, E42, E45, E50, E55, E60, Exx means solutions of water and ethanol with an ethanol concentration at 40, 42, 45, 50, 55, 60 and xx vol % ethanol, respectively.

5. BRIEF DESCRIPTION OF THE DRAWINGS

FIG. 1. The interaction between wheat lipids and water as described by this ternary phase diagram determined at room temperature by equilibrating mixtures of polar and non-polar wheat lipid components with water. The phases are described in the text.

Figure 2:
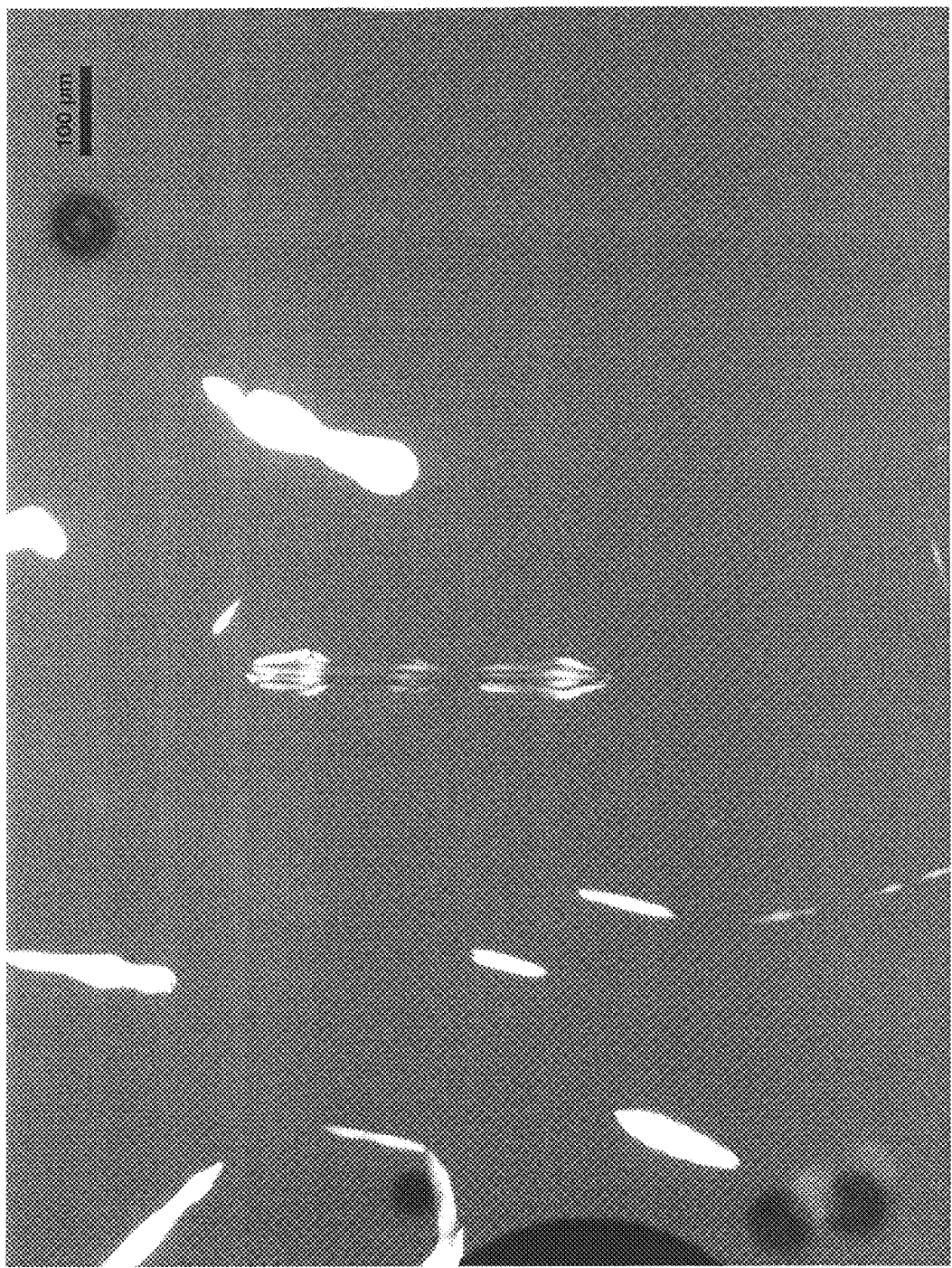

FIG. 2. The T2 stem solution viewed in the polarizing microscope. Birefringent particles with characteristic so-called batonnet shapes are seen in equilibrium with the isotropic fluid.

Figure 3:

FIG. 3. The picture is taken after addition of a small amount of water, but below the limit of swelling, to the same fluid as shown in FIG. 1. The added water induces a transformation into the HII-phase both within the batonnet that is shown and in the surrounding outside fluid. The water swelling inside the original batonnet results in a transition into the HII-phase, with its characteristic strong birefringence interference colors.

Figure 4:
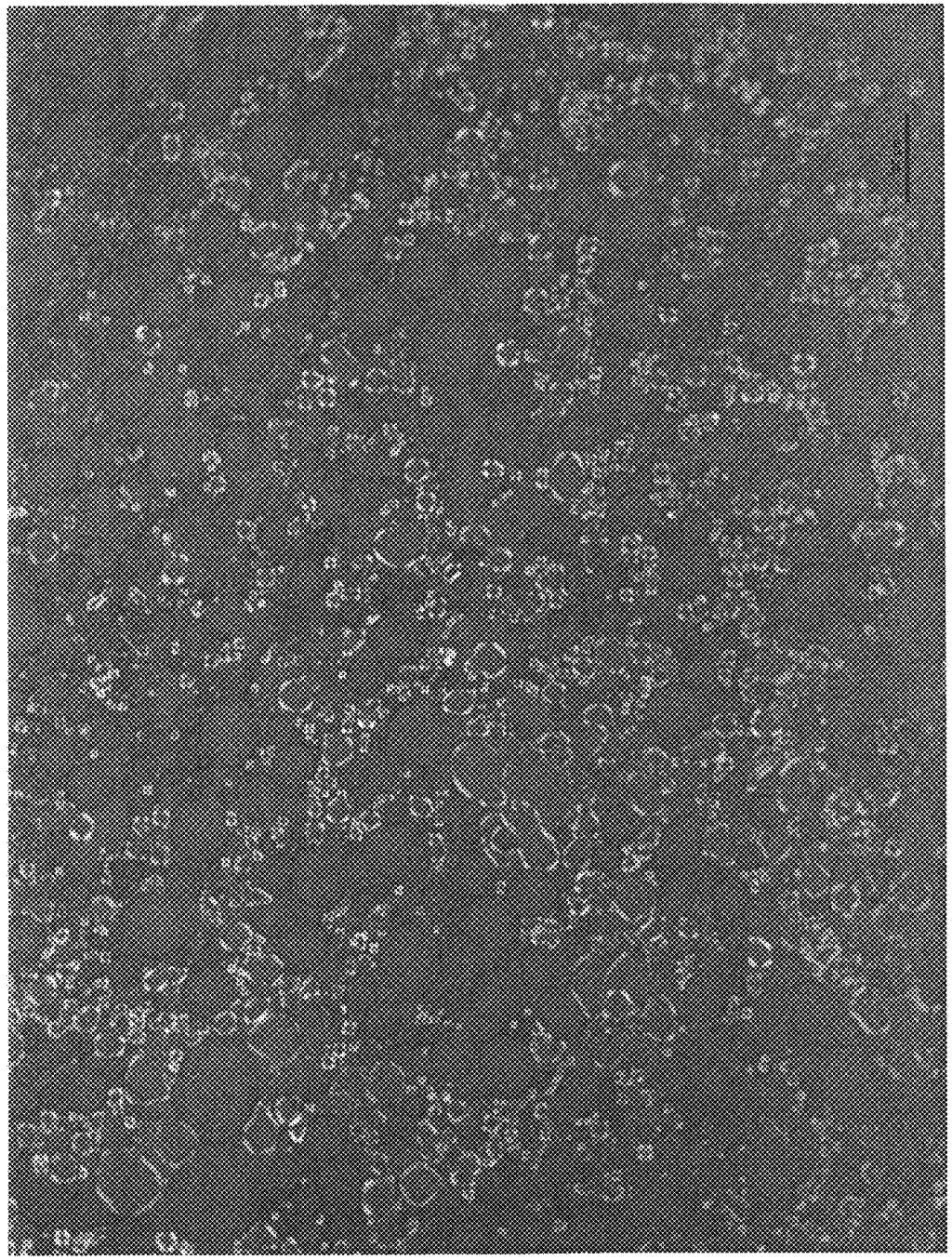

FIG. 4. A liposomal dispersion of the T7 stem solution was diluted to an ethanol-water composition of 55:45 (v/v) and a lipid content of 10% (w/w). Only textures characteristic for the L-alpha phase is seen, with liposomes showing Maltesicross textures.

Figure 5:
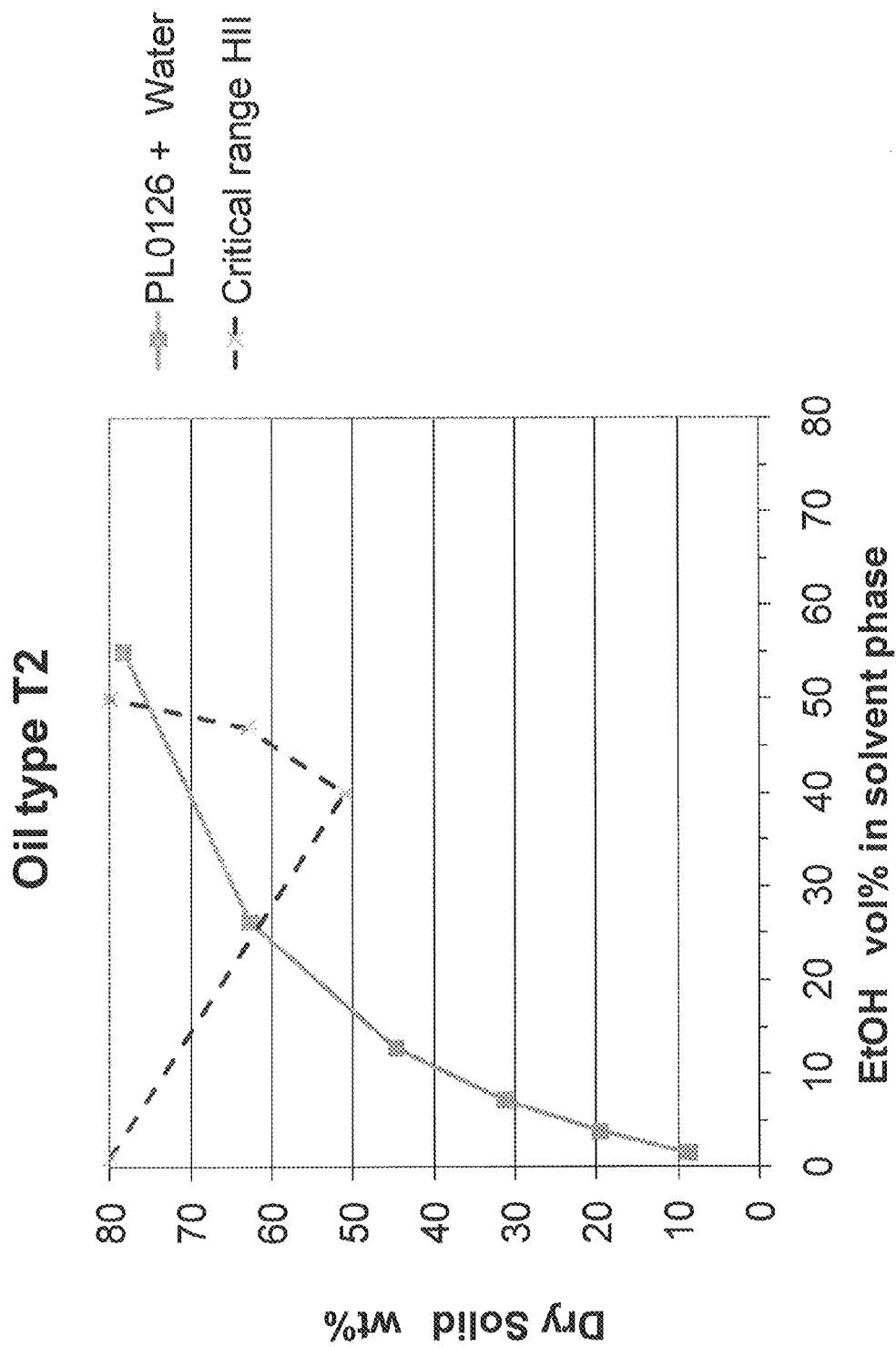

FIG. 5. The Dry Solid in wt % vs EtOH vol % in solvent phase for PL0126 when diluted with water. The borderlines for the "HII-phase formation" range are given. Note that the composition of the oil passes through the HII-range during dilution with water and that the process line is not a straight line using these units.

Figure 6:
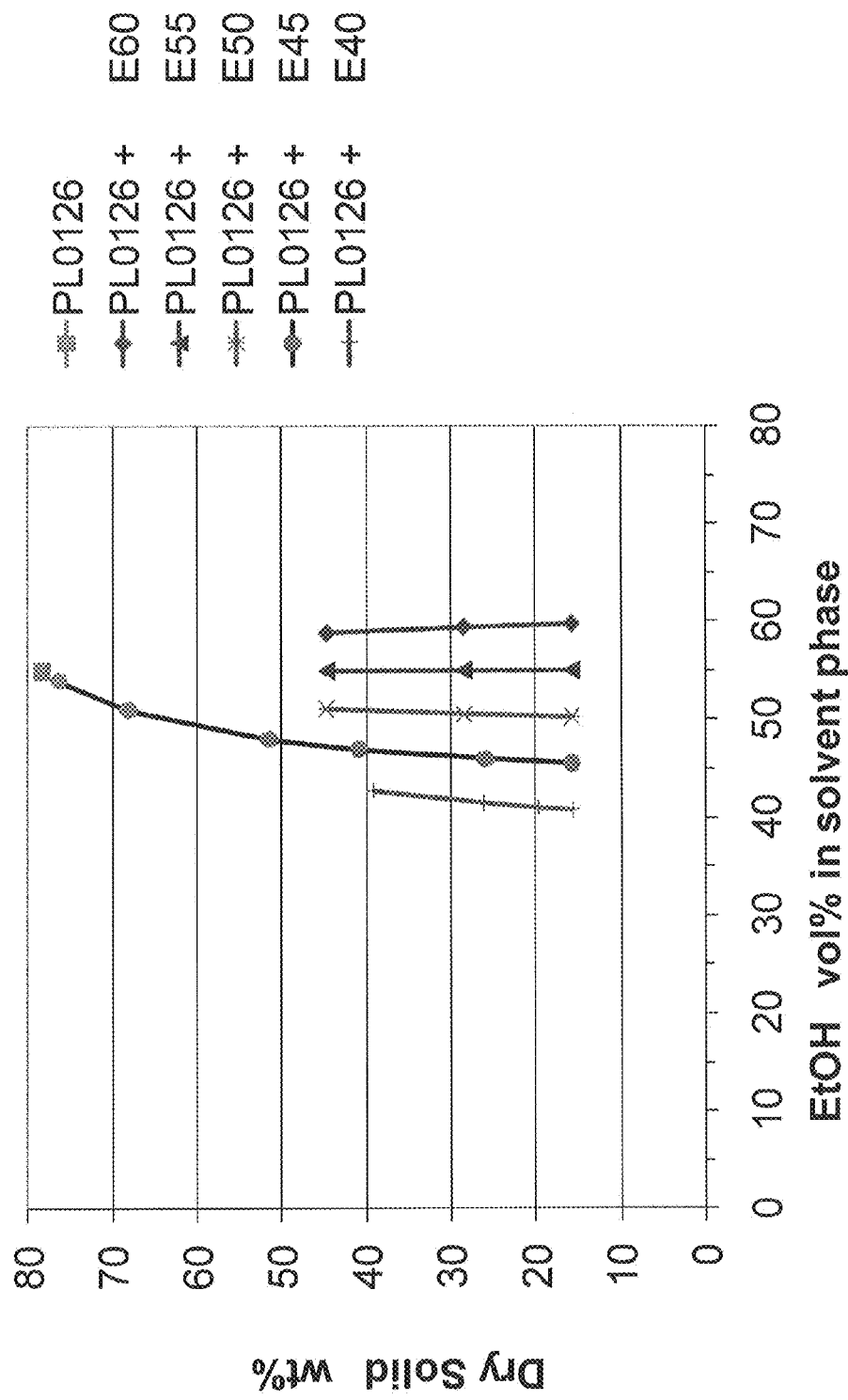

FIG. 6. The Dry Solid in wt % vs EtOH vol % in solvent phase for PL0126 when diluted with different solutions of ethanol and water where the ethanol concentration range from 40 to 60 vol %. Note that the process lines are is not a straight line using these units.

Figure 7:
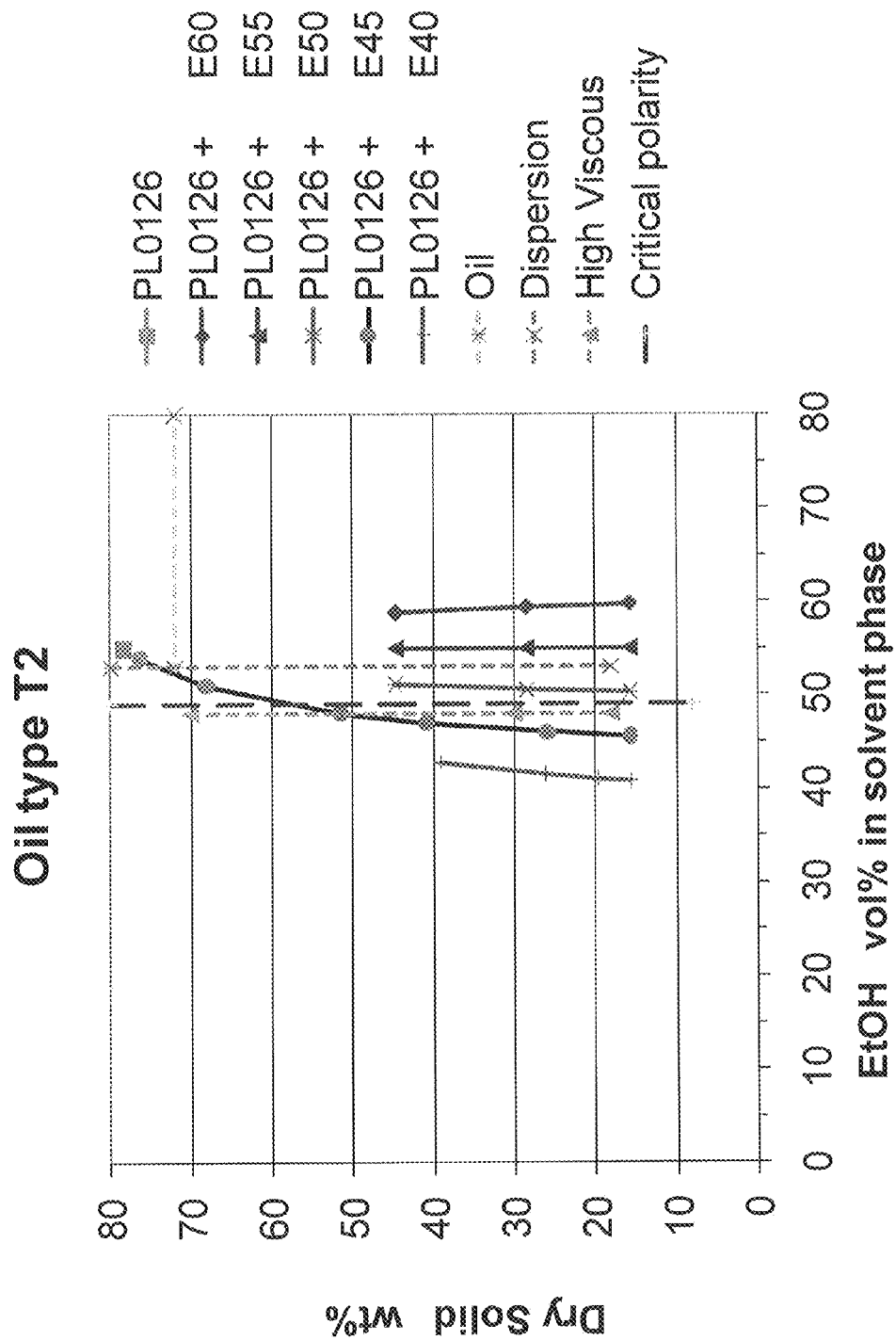

FIG. 7. The same as FIG. 6 but the borderlines for the "Oil phase" range, the "Dispersion" range and the "High Viscous" range and the "Critical polarity" of PL0126 are included.

Figure 8:
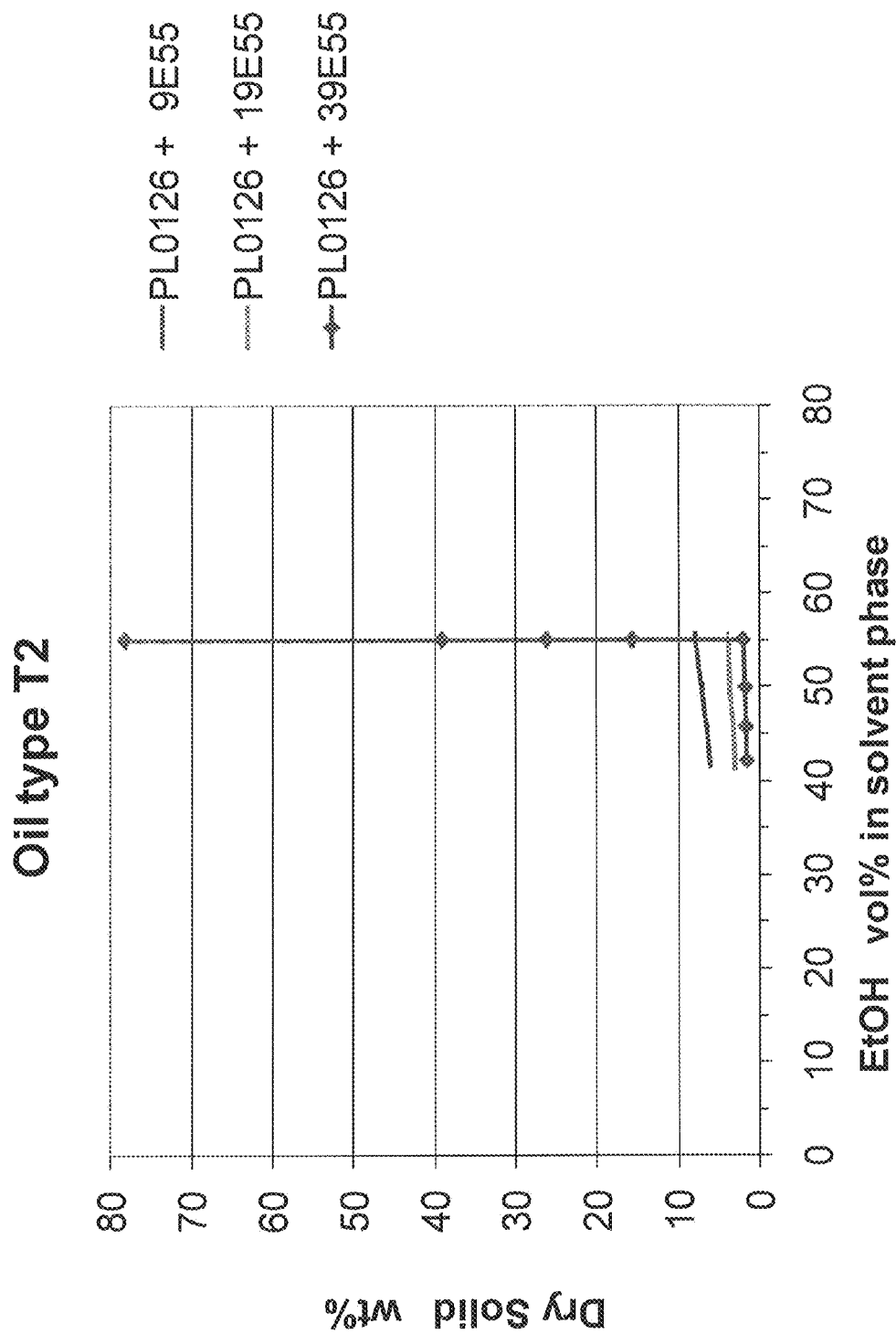

FIG. 8. The Dry Solid in wt % vs EtOH vol % in solvent phase for PL0126 when first diluted with 9, 19 and 39 parts of E55 and then water is added to these mixtures.

Figure 9:
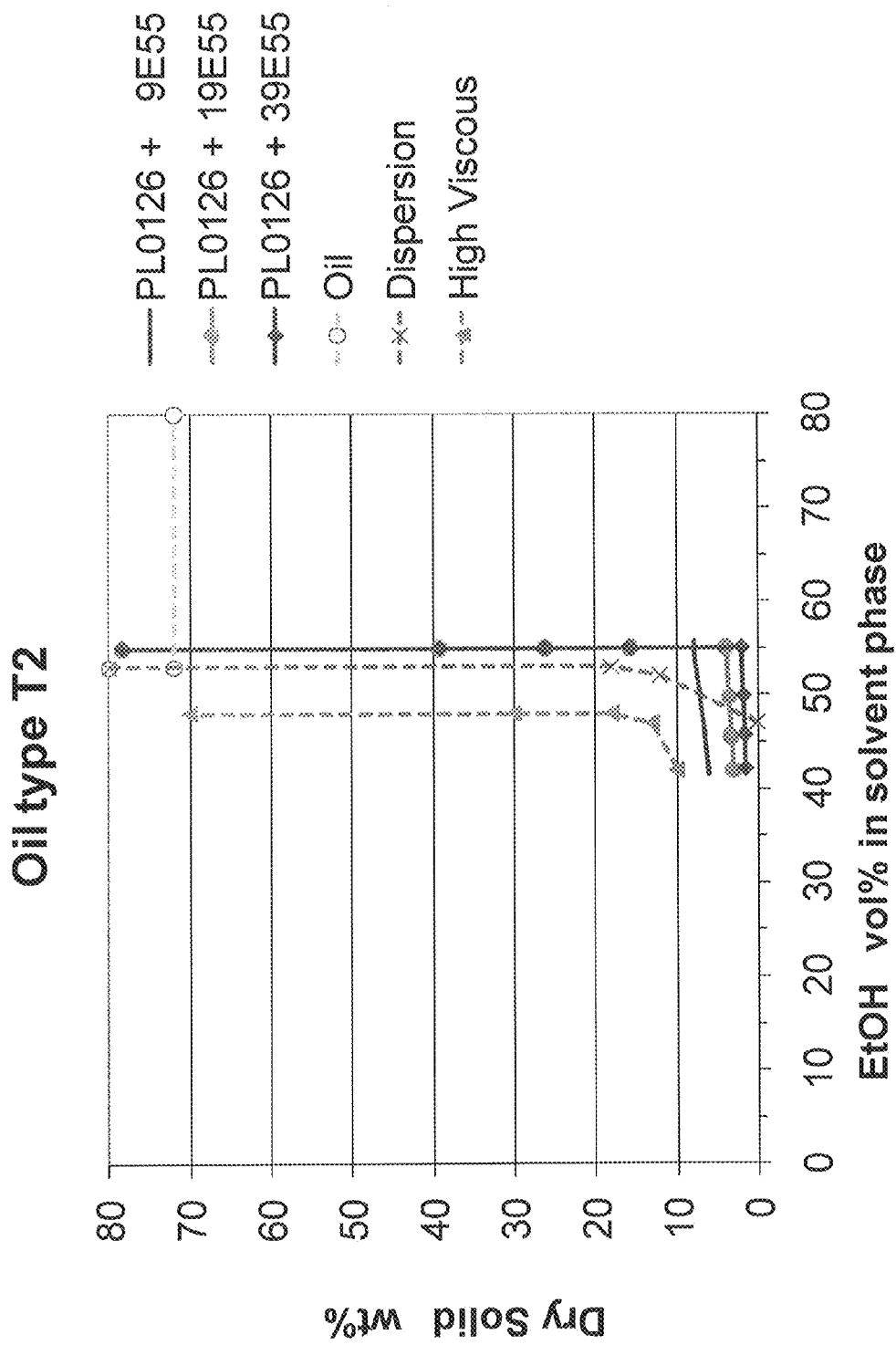

FIG. 9. The same as FIG. 8 but the borderlines for the "Oil phase" range, the "Dispersion" range and the "High Viscous" range are included.

Figure 10:
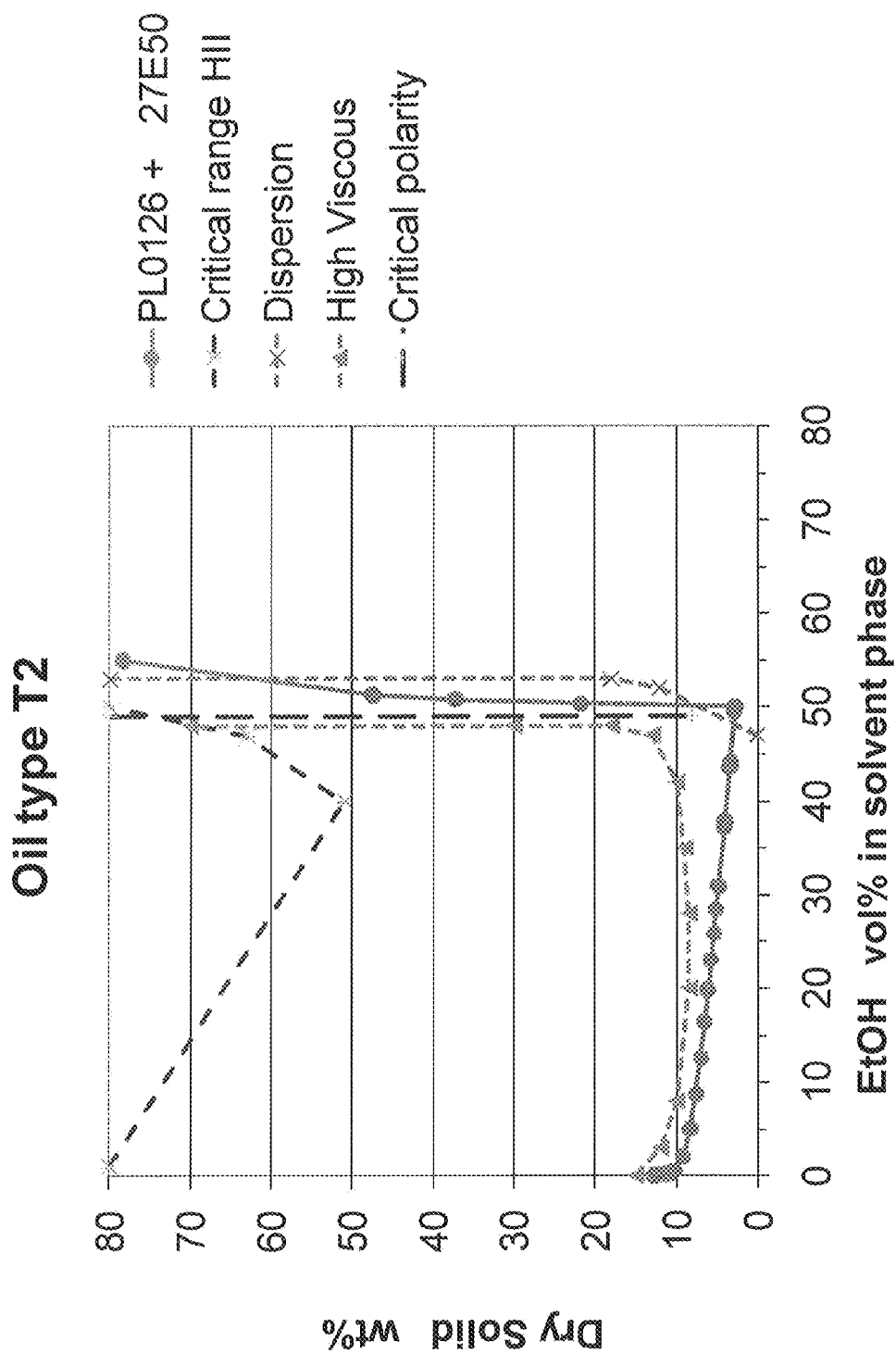

FIG. 10. The Dry Solid in wt % vs EtOH vol % in solvent phase for PL0126 when first diluted with 27 parts of E50 and then the ethanol is removed by evaporation using a batch process.

The borderlines for the "High Viscous" range, the "Dispersion" range, the "HII-phase formation" range and the "Critical polarity" for PL0126 are included.

Figure 11:
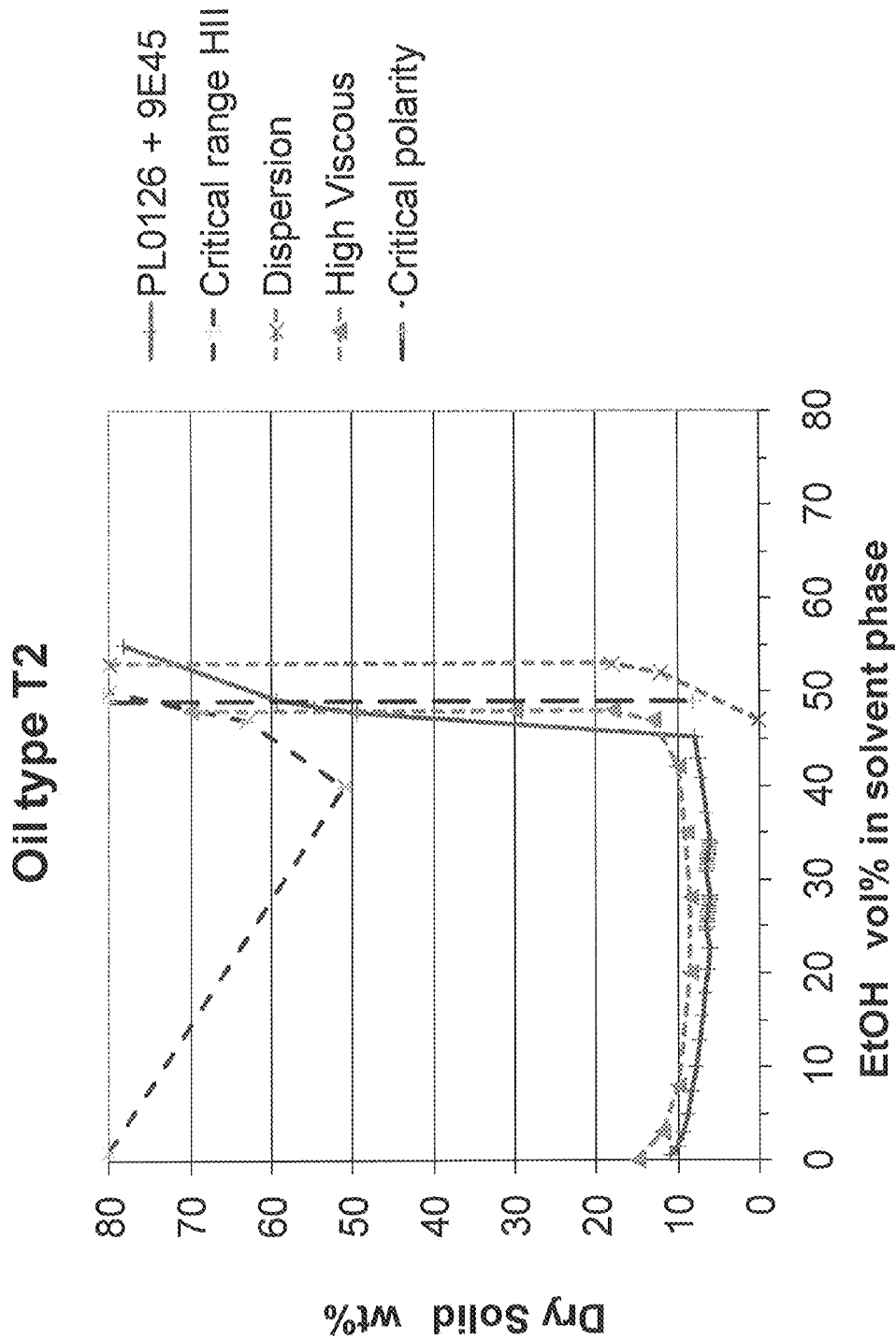

FIG. 11. The Dry Solid in wt % vs EtOH vol % in solvent phase for PL0126 when first diluted with 9 parts of E45 and then the mixture is diluted with water and the ethanol is then removed by evaporation using a batch process.

The borderlines for the "High Viscous" range, the "HII-phase formation" range and the "Critical polarity" for PL0126 are included.

Figure 12:
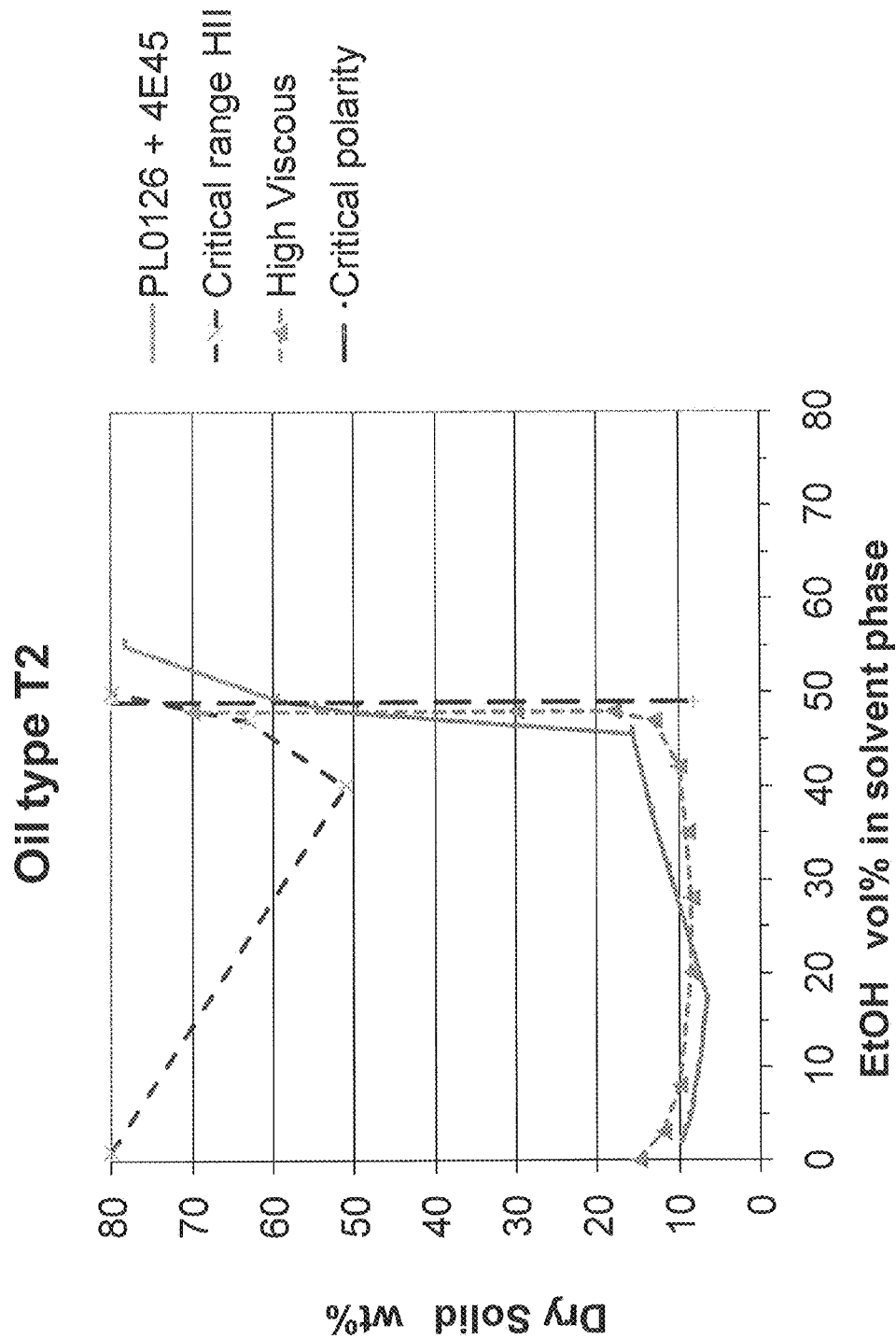

FIG. 12. The Dry Solid in wt % vs EtOH vol % in solvent phase for PL0126 when first diluted with 4 parts of E45 and then the mixture is diluted with water and the ethanol is then removed by evaporation using a batch process.

The borderlines for the "High Viscous" range, the "HII-phase formation" range and the "Critical polarity" for PL0126 are included.

Figure 13:
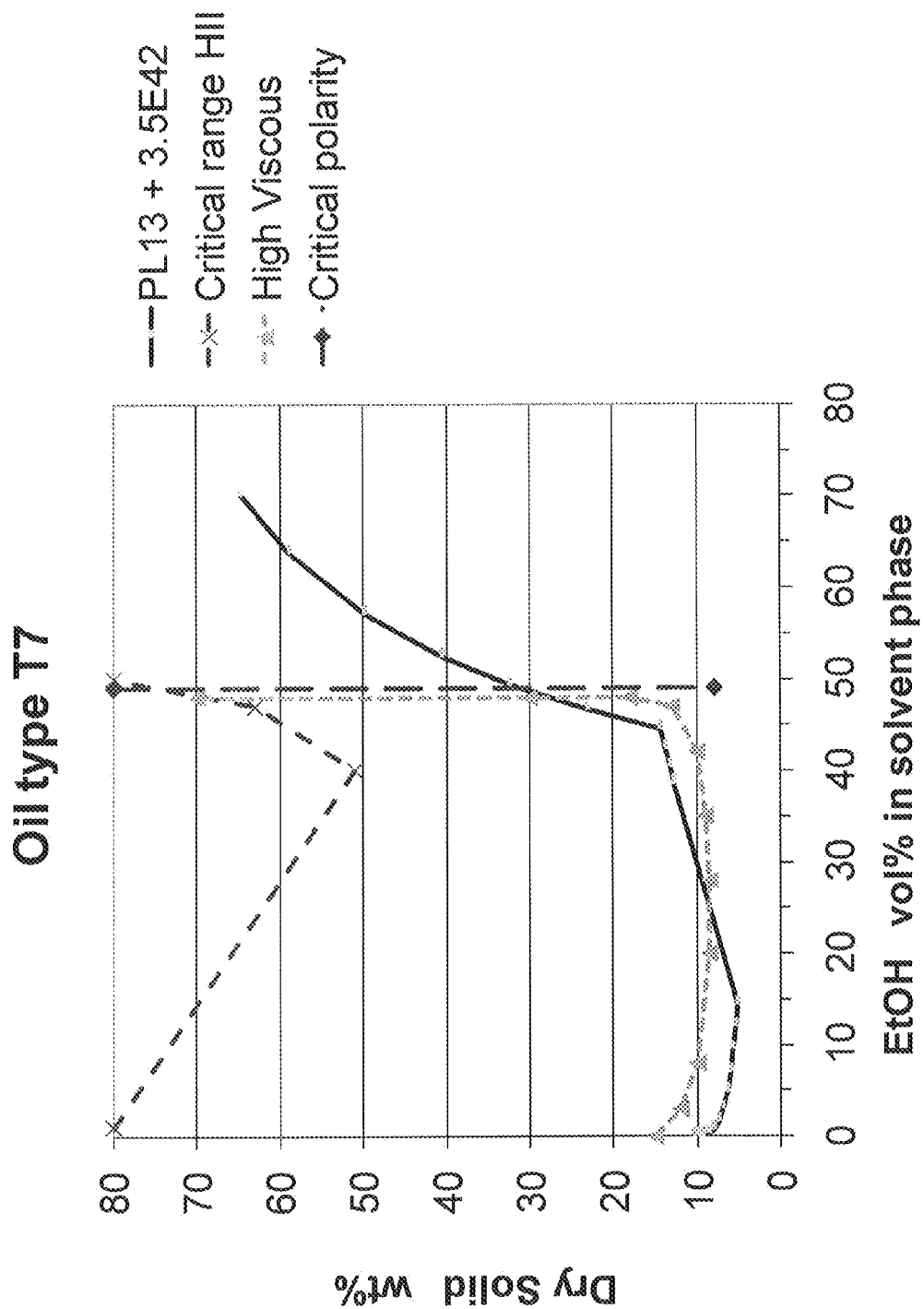

FIG. 13. The Dry Solid in wt % vs EtOH vol % in solvent phase for PL13 when first diluted with 3.5 parts of E42 and then the mixture is diluted with water and the ethanol is then removed by evaporation using a batch process.

The borderlines for the "High Viscous" range, the "HII-phase formation" range and the "Critical polarity" for PL13 are included.

Figure 14:
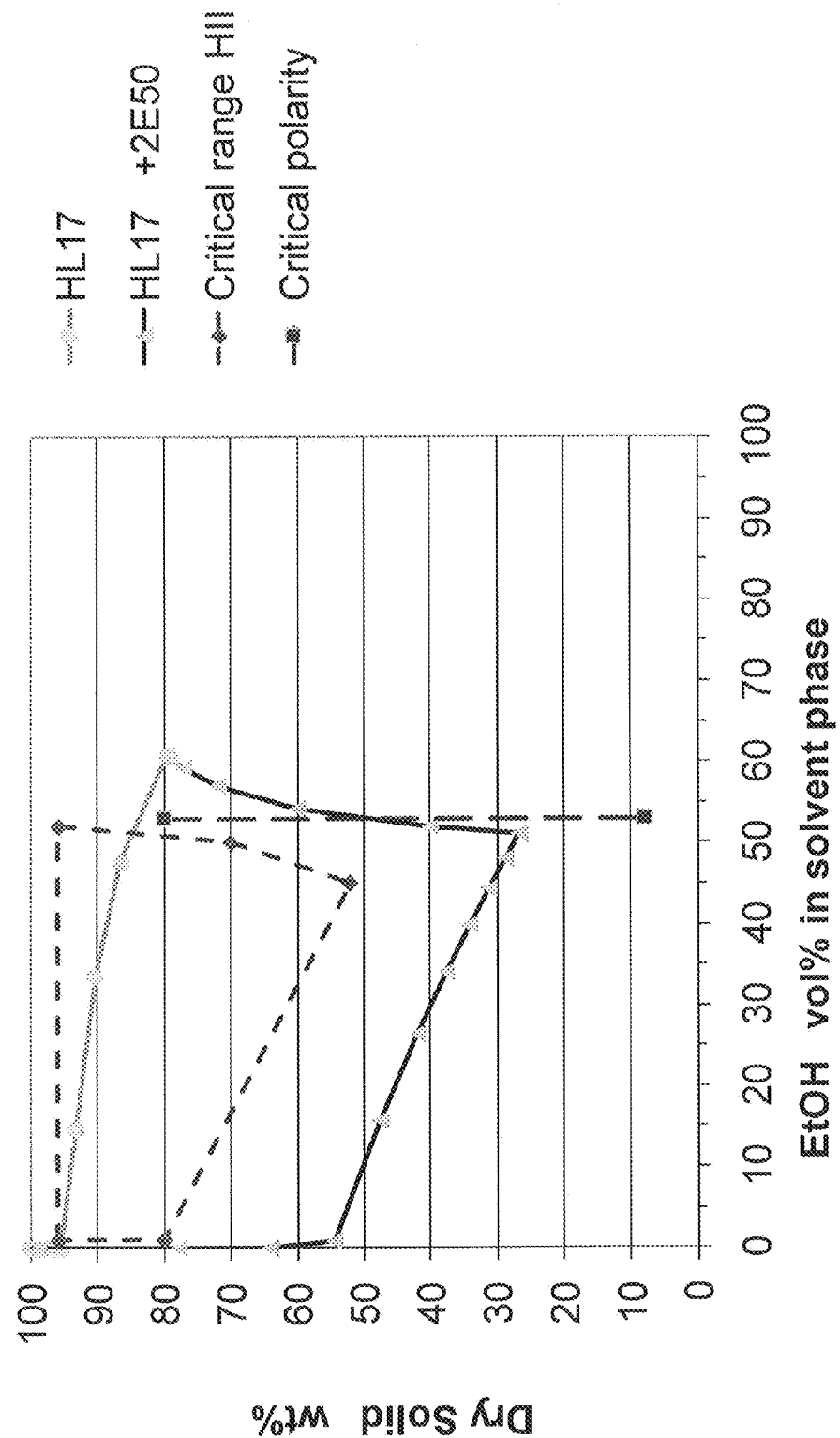

FIG. 14. The Dry Solid in wt % vs EtOH vol % in solvent phase for two processes. The first process line describes when the ethanol in HL17 is directly removed by evaporation using batch processes. The second process line describes when HL17 is first diluted with 2 parts of E50 and then the ethanol is removed by evaporation using batch processes.

The borderlines for the "High Viscous" range, the "HII-phase formation" range and the "Critical polarity" for HL17 are included.

FIG. 15. The Dry Solid in wt % vs EtOH vol % in solvent phase for SPO10 when first diluted with 2 parts of E45 and then the mixture is diluted with water and the ethanol is then removed by evaporation using a batch process.

The "Critical polarity" for SFO10 is included.

6. DETAILED DISCLOSURE OF THE INVENTION 6.1 Summary

Extensive studies have been devoted to oat lipid fractions and the possibility to produce aqueous dispersions of such fractions for food and pharmaceutical applications. During this first phase of our work it was realized that the preparation method, careful dilution of the oil using solvent mixtures of ethanol and water, also can be used in order to produce dispersions, vesicles, liposomes, emulsions and oils, of other mixtures of galactolipids and phospholipids. Furthermore, the process can be applied to mixtures of these lipids with monoglycerides in order to prepare dispersions of cubic liquid-crystalline phases in water.

Both lipophilic and hydrophilic active ingredients can be incorporated in the different types of lipid particles and used in order to increase bioavailability of important nutrients.

The particle dispersions can be mixed into food or used as they are as so-called shots. The particle dispersions can also be used in pharmaceuticals, cosmetics, agrochemicals and feed mixed with other components or used alone.

An early study of the effect on satiety of the lipid particles based on galactolipid rich fractions has been performed. The outcome from two breakfasts studies can be summarized in this way: one day the lipids came from vesicles made from oat oils and the second day the lipids originated from milk. Clear indications of positive effect on satiety were obtained from GLP-1 levels in blood samples.

6.2. Introduction

Ethanol-water solutions of lipids as dealt with in this invention have obvious advantages compared to other systems involving organic solvents when dealing with foods or pharmaceuticals, and important applications involve processes in order to form aqueous lipid dispersions. One example is preparation of liposomes by the ethanol injection method.

The process presented here allows better control of the initial stage of such phase separation processes, and therefore reproducible conditions in formation of uniform particle dispersions are created with this invention.

6.3. Part I The Step-Wise Water/Ethanol-Dilution/Ethanol-Evaporation Process Applied in Oat Lipid System.

In order to describe the application of the invention for preparation of vesicle dispersions of oats, it is necessary to go back to the phase diagram shown in FIG. 1. As can be seen from the one-phase regions in FIG. 1, the addition of water to a lipid composition where the concentration of polar lipids exceed 65 lipid % first gives the hexagonal HII-phase, and above about 18% (w/w) of water the lamellar L-alpha phase is formed. In the same way when fractionated oat oils according to this invention, with a concentration of polar lipids above 50%, are mixed with water, a HII-phase is formed and the resulting HII-phase creates a very strong gel. Once formed it is very stable and impossible to disperse into small particles, see Example 1.

We have developed an ethanol-water dilution/evaporation process with main purpose to avoid the formation of the HII liquid-crystalline phase if the lipids first are exposed to water. If the ethanol concentration in the ethanol-water mixture used to dilute the oil exceeds about 30% (v/v), no HII-phase is formed (as seen in FIG. 4 which is considered later). Thus, we first add a water-ethanol mixture with about 45 vol % ethanol to the stem solution. Then, after enough solvent has been added into the liquid-crystalline L-alpha phase via this ethanol-water solution, we have found that it is possible to add pure water to the mixture. In this way we could circumvent the HII-phase and create and dilute the L-alpha phase without forming the irreversible gel-state and the L-alpha-phase initially formed at water-in-ethanol addition persist all the way towards the transition with excess of water into a unilamellar vesicle dispersion. The ethanol added can be removed by evaporation and the particles are very small and the dispersion becomes very stable.

In addition to this, it was interesting to notice that this process spontaneously created very small and uniform particles. These size characteristics of the dispersion was achieved when the dilution of the oil is performed using a water-ethanol mixture with an ethanol concentration close to the critical concentration, se definitions. When the ethanol concentration is higher than this transition-point, the solvent phase is filled with large liposomes. These particles are not stable. When water is added to this mixture the addition rate and the mixing rate of water become very difficult to control and the particle size distribution will be wider. If the ethanol concentration is considerably lower than this transition-point, the formation of particles is slower and larger particles are formed. If the ethanol concentration is much lower than the transition point, large gel particles are formed. Once formed these particles are very stable and it is very difficult to reduce the size of these particles using mechanical energy. Thus, at a suitable ethanol concentration the particles are formed spontaneous very fast and the particles become very small.

Another way to illustrate these phase changes during water-dilution-ethanol-evaporation that takes place is that we again start from the phase diagram in FIG. 1. We can imagine a fourth dimension in the upwards direction corresponding to the ethanol component, forming a corner in a tetrahedron describing phase regions in a four-component system. Thus we have found that there is a "corridor" at increasing ethanol addition between the existence range of the HII-phase and the ethanol-water solution of these lipids (T2 or T7) which we utilize in the preparation process, which makes it possible to form the L-alpha phase directly (and then the vesicles are formed very rapidly) without passing the HII liquid-crystalline phase.

6.3.1 Starting Materials of Oat Lipids

We will describe in detail two different suitable starting materials for the dispersions, representing extreme proportions of non-polar:polar lipids. They are oat oil fractions, fractionated using ethanol, water and sugar according to the principles described WO2010104444. In that document the fractions are called "Heavy Polar Lipids" and "Low in Estolides". In this document they are called stem solutions T2 and T7, respectively. The compositions of these fractions are described in Table 1.

Crude oat oils contain about 15 wt % polar lipids. These polar lipids are rich in galactolipids and particularly in di-galactosyl-di-acyl-glyceride (DGDG). The term "rich in galactolipids" refers to that at least 30 wt % of the polar lipids are galactolipids. The oat DGDG is unique because some of the DGDG contains one or more unsaturated hydroxyl-fatty acids, which are esterified by other fatty acids. Molecules containing fatty acids with esterified hydroxyl-fatty acids are called estolides. Natural estolides exists only in oats (WO 88/08253, Jee M. H. 1995, "A new emulsifier from oat", Proc. 21$^{st}$ World Congress ISF, The Hague, paper 135). Synthetic estolides are common, e.g. products based on castor oil, or other synthetic emulsifiers like PGPR.

6.3.2 Preparation Process of the Unilamellar Vesicles Dispersions of Oat Lipids

When the stem solutions T2 or T7 are mixed with water a very viscous gel is formed. Once formed this gel is cannot be dissolved, either by heating up to 100° C. or stirring. A schematic diagram based on this gel formation is shown in FIG. 5. The gel is formed when the concentration of ethanol in the solvent phase becomes lower than about 40 vol %.

However, as described above it was found that it is possible to avoid formation of this gel, by careful dilution of the oil in an ethanol containing solvent, see FIGS. 6-7 and FIGS. 10-13. An ethanol concentration in the range of 40-55 vol % is suitable in most cases. If the ethanol concentration is too high the oil will not be dispersed. If the ethanol concentration is slightly too low the rate of particle formation is slower and the particle size distribution will be broader and some particles larger than 1 μm will be formed. If the ethanol concentration is much too low, gel particles (which is a HII-phase) will be formed as mentioned above. Once formed, they will remain as large particles (>1 μm). Particle dispersions are formed by the polar lipids and water. The ethanol can be removed by evaporation. When the ethanol is removed the particles become very stable and the dry solid can be increased. However, when the dry solid content exceeds 10 wt % the viscosity increases rapidly.

The gel described here phenomenological was identified in the polarizing microscope by its birefringence texture as an HII-phase, as further described below.

The composition of the T2-fraction is described in Table 1. Stem solution T2 looks like a homogeneous oily phase with high viscosity. However, in a polarizing microscope, beautiful rod-shaped particles are seen which are strongly birefringent, as shown in FIG. 2. Their presence and orientation at flow explain the viscous properties of the fluid. Such particles were first described in 1910 by Friedel and Grandjean, and termed batonnets (in French—and later this name is used also in English) due to the regular elongated shape with mirror symmetry over a middle-axis. Such liquid-crystalline particles have been shown to consist of stacks of soft lamellae of uniform thickness. The geometric packing constrains of such curved lamellae induce the so-called focal-conic texture, which explains the outer particle shape as seen in the polarizing microscope. This lamellar structure has also been termed smectic in the literature. The ordered molecules at the particle surface exist in dynamic equilibrium with disordered molecules in the outside isotropic fluid.

As far as we know, this is the first observation of batonnets in natural lipids.

The liquid-crystalline phases occurring in aqueous systems of polar lipids have been well characterized since their first description in the 1960s. They consist of interfaces formed by the polar heads arranged in different geometrical patterns, separating hydrocarbon chain regions from aqueous regions. Their structures are lamellar, hexagonal and cubic, with the phases L-alpha and HII utilized in the present invention being the most common two phases. As these liquid-crystalline phases contain water (or a solvent) they are termed lyotropic liquid crystals. When ethanol is present in the water medium, it could be expected that there is a treasure concentration of ethanol for this type of phase behaviour, and above this concentration no aqueous regions are formed. This is considered to represent the structure of the fluid phase at 65% of ethanol, which are the stem solutions we are using. In such a fluid a different type of liquid-crystalline phase can then crystallize. This is a thermotropic liquid-crystalline phase consisting of lipid molecules, only without any inside region of solvent molecules. This phase exists in equilibrium with the outside isotropic solution, with its laminar structure, forming the batonnet organization shown in FIG. 2.

When water is added to T2, the gel-like HII-phase is first obtained. It is very viscous and it is not possible to disperse it in water. Furthermore heating up to about 90° C. shows no effect on its stability or water swelling. In the microscope it can be seen that this phase is very homogeneous and strongly birefringent, exhibiting strong interference colors covering the visible spectrum. All these features are consistent with the well-known characteristics of the HII-phase.

If the water dilution process of the T2 stem solution only involves a limited amount of water, it can be seen in the microscope how parts of the isotropic oil phase as well as the inside of batonnets are transformed into the HII-phase, as indicated by the strong interference colors within the birefringent regions, as shown in FIG. 3.

When the L-alpha phase is formed directly at water-ethanol swelling of the T2 stem solution, at a certain ethanol concentration (above about 50% (v/v)), it shows low viscosity and a weak and uniform birefringence without interference colors. At further dilution in ethanol-water solution, a liposomal dispersion is obtained, as shown in FIG. 4.

When the T2 stem solution is exposed to an excess of a solvent phase rich in water, via the described water-ethanol dilution/ethanol evaporation process, the T3 type of dispersed lipid particles is obtained as described in example 3 below.

These particles are remarkably stable without any sign of separation (sedimentation or creaming) during storage. Studies by cryo-transmission electron microscopy (cryo-TEM) and X-ray synchrotron diffraction of these kinetically stable dispersions containing 1 and 10% (w/w) lipids in water (and less than 1% ethanol) showed a quite uniform structure of the vesicles. There was a dominance of vesicles within the vitrified water film in the size range 40-50 nm in diameter). This dominating size distribution showed a uniform bilayer structure, some of the vesicles showed a pseudo-hexagon shape, which appeared to be an effect of particle-particle interaction in the cryo-TEM film. A synchrotron small-angle X-ray scattering analysis confirmed the small size distribution and showed no indication of shapes beside spherical ones. There was a peak at 5.2 nm, which is interpreted as due to the lipid bilayer thickness. Another was also a very small hump at about 2.2 nm, which is assumed to reflect the water layer thickness in a small fraction of particles with two or more bilayers (also seen in cryo-TEM).

The composition of T7 is described in Table 1. Like the stem solution of T2, also T7 stem solution appears homogeneous regarded by the naked eye, but shows birefringent batonnet particles in the isotropic fluid in the polarizing microscope. When this fraction, containing a higher proportion polar lipids, is diluted according to the same process as used in fraction T2, however, a higher proportion of liposomes take part in the formation of the final dispersion. At dilution to a lipid concentration of 10 wt % and an ethanol concentration of 55 vol %, there is a striking dominance of liposomes, as shown in FIG. 4.

Thus the unilamellar vesicles that are spontaneously formed by this preparation process are remarkably uniform in size and quite small, compared to vesicle size distributions reported in the literature. By ultrasonification, however, small unilamellar vesicles can be produced, as demonstrated early for example in the case of dimyristoyl-phosphatidylcholine (B Lentz, T J Carpenter, D R Alford: Biochemistry 26 (1987) 5389-5397). The small size may provide an important advantage in the applications that we consider.

6.3.3 Mechanisms During Formation of the Very Small Particles

Why are the vesicles formed spontaneously so fast so small? We think that the size reflect a segregation of the available lipid molecules according to their molecular shape. Thus the inner monolayer of the vesicle bilayer could be enriched in lipid molecules with a larger cross-section area at the methyl end group region, with molecules like the DGDG estolides. The outer monolayer on the contrary could be enriched in molecules with an opposite molecular shape, with larger cross-section area at the polar head group region compared to the methyl end group region, for example digalactosyl-monoglycerides. Another unusual feature is that these vesicles in the case of the T2 stem solution contain a rather high proportion of triglyceride molecules, about 30 lipid %, which seems to be solubilized within the bilayer.

We propose that it is the different composition of the lipids creating the liposomes and the favourable conditions close to the critical polarity that are the reasons for the dramatic almost spontaneous change in particle size between the liposomes occurring during dilution at conditions close to the critical polarity. At a polarity below the critical polarity no or very small amounts of estolides and triglycerides are dissolved in the solvent phase and therefore not included in the liposomes. This leads to a diameter of the liposomes in the range of 1 to 40 µm.

We propose that the rapid disintegration of the particles from the range 1-100 µm at a polarity slightly below the critical polarity to below 100 nm slightly above the critical is due to composition of the lipids that create the driving force in combination with a suitable concentration of ethanol in the whole system that is providing a low viscous solvent phase that facilitate mass transport and a suitable polarity where this transition can occur very easily.

The conclusions from Examples 2, 3 and 4 are that:
The critical polarity can be determined using the principles described in Example 2.
The best particle size distribution is achieved when the oil is diluted with a first ethanol-water solvent with a polarity slightly higher than the critical polarity, see FIGS. 10 and 12. In this way a high viscous product is achieved due to rapid formation of very small particles. The dilution with this first ethanol-water solvent mixture should proceed until the viscosity reaches a maximum. Then, the achieved particle size distribution can be maintained and the ethanol can be removed by addition of water followed by evaporation. The amount of added water should be sufficient to allow the following evaporation to allow the product to reach below an acceptable concentration of the ethanol and at an acceptable viscosity of the final product.
The final product had a dry solid content of 10 wt %; the content of ethanol was below 0.1 wt % and for the best process the resulting unilamellar vesicles were in the range of 40-50 nm.

The very small particles and the very narrow particle size distribution is thus also due to that the lipids only get in touch with a solvent phase with a very specific concentration of ethanol close to the critical concentration.

Note that the small difference between E50 and E45 gave rise to an important difference in particle size distribution, see Example 6. This difference is decisive weather the vesicles can be mixed into other products without problems or not and if the particle structure will remain unchanged when they have passed the stomach and reached the intestine.

6.3.4 Formation of Oil High in Polar Lipids without HII and Ethanol Using the Ethanol-Water Dilution/Evaporation Process.

When the solvent in oat oil with a polar lipid concentration of about 70 lipid %, like T2, is evaporated, the oil becomes very viscous and impossible to handle. When the polar lipid concentration is reduced to about 40 lipid %, the viscosity is reduced and the oil is possible to handle. However, in some cases the emulsifying capacity is dramatically reduced. When we investigated the oil in microscope we saw HII crystals. These HII particles are responsible for the very high viscosity observed and the reduced emulsifying capacity observed.

In this invention we show that, by using the ethanol-water dilution/evaporation process, oils containing galactolipids can be free from HII crystals and the oils remain easy to handle and the oils keep their high emulsifying capacity also after removal of the ethanol, see Example 8.

The product in the example contained less than 1% wt ethanol and less the 3 wt % sugar. When this oil is exposed to water it is forming less hexagonal phase than lamellar liquid-crystalline phase during a following water swelling process, which results in a spontaneous emulsification. We expect that a reduction of the sugar concentration in the oil to less than 2% sugar may improve the emulsification properties even further. We also expect that the concentration of polar lipids should be more than 25 wt % polar lipids, preferably more than 30 wt % polar lipids, and that the polar lipids from oats is particularly suitable.

This means that downstream processing using lipids containing galactolipids becomes easier to run. This will result in products with smaller particles, more even particle size distribution and more reproducible product quality compared to traditional evaporation methods.

6.4 Part II The Step-Wise Water/Ethanol-Dilution/Ethanol-Evaporation Process Applied in More Complex Lipid Systems The step-wise water-ethanol dilution/ethanol-evaporation of the ethanol-water solution of the oat lipid fractions, described above, can also be applied in order to prepare particles of bicontinuous cubic phases. This process makes possible improved control of particle size distribution by sequential co-precipitation of an L-alpha-phase, together with a cubic phase. The particle size is controlled by the kinetics of the build-up of surface zones of the particles.

In order to explain how our process can be applied in such cases, we will consider the preparation of cubic particles from oat lipid—monoolein mixtures and we start from monoolein solved in ethanol-water system, where preparation of cubic particles was based on the ternary phase diagram monoolein-water-ethanol as reported by Spicer and coworkers (Spicer et al. 2001, Langmuir, 17, 5748-5756). The first ternary phase diagram of this system was mapped by Engstrom et al. (S. Engström, K. Alfons, M. Rasmusson, H. Ljusberg-Wahren: Progr. Colloid & Polymer Sci. 108 (1998) The Colloid Science of Lipids Kåre Larsson Festschrift pp 93-98).

There is a small three-phase region in the phase diagram where the cubic phase co-exists with the L-alpha phase. They start from monoolein dissolved in pure ethanol and by dilution towards the water corner using pure water, cubic particles will crystallize from the liquid ethanol-water phase at passing into the three-phase region. This is in short the preparation process as described by Spicer et al (Spicer et al. 2001, Langmuir, 17, 5748-5756; WO02068561, WO02068562, WO0202716).

If instead the process according to the present invention is used, we achieve an ethanol-water-monoolein mixture of about 20:20:60 wt % by mixing monoolein with an ethanol/water mixture of 50%. This mixture is then mixed with an ethanol-water mixture of about 30 wt % ethanol. The exact ethanol concentration in this stage is determined in a way analogous to the procedure described in Example 2. The amount of the ethanol and water mixture added is determined in analogy to that given in Example 3. Finally, water is added and if required ethanol is evaporated in analogy to the description in Example 4. These conditions are pre-determined and adjusted by trial and error and can then be applied in a reproducible way in large scale processes.

A useful concept in our preparation process is the critical polarity which defines the concentration of ethanol and water when a water-in-oil emulsion is transformed into an oil-in-water emulsion when the polarity is increased, see definitions. At water concentration in the added solvent medium slightly above the critical polarity has been observed to give ideal condition for initiating the precipitation of the cubic particles.

At the critical polarity for an oil-water interfacial monoolein film formation should be expected to induce nucleation of the liquid-crystalline phases. This might be one reason for the improved possibilities to produce uniform particles by this process, as the passage of the liquid crystal phase boundaries can take place slowly in a controllable way. Water addition directed towards the water corner will result in a faster and less controllable precipitation. This difference will be particularly important in large scale process.

We will also consider here the mixed systems of phosphatidylcholine and monoolein, which was the system where cubic particle formation first was demonstrated (K. Larsson: J. Phys. Chem. 93 (1989) 7304-7314). About 10% (w/w) of a pure phosphatidylcholine from soy bean oil in monoolein is enough for formation of a more uniform particle size distribution of cubic particles and, more important, to increase their stability against aggregation.

In this invention we propose by careful dilution close to the critical polarity. Then the separation into an L-alpha phase has started. At the following dilution with the second ethanol-water mixture until the phase separation into also the cubic phase has been fully obtained in dispersed form. Then the ethanol is evaporated.

6.5 Part III Formation of Emulsions Using the Ethanol-Water Dilution/Evaporation Process The starting lipid material we use comprises galactolipids as a polar lipid component. Galactolipids are very efficient emulsifiers. They are naturally present in the original oat oil ethanol extract and they can produce an oil-in-water emulsion when the non-polar lipid concentration is about 50 up to 95 lipid % by applying our ethanol-water-dilution/ethanol-evaporation process. At lower concentration of non-polar lipids liposomes are formed by applying our ethanol-water-dilution/ethanol-evaporation process. However, galacolipids may form HII-particles, which may by formed using traditional methods to produce emulsions. Once formed, oil containing HII-particles has lost most of its emulsifying properties.

With the principles in this invention, ethanol-water-dilution/ethanol-evaporation process, we can avoid the formation of HII-particles in oils containing galactolipids. With these methods the full potential in the lipids are utilized, see Example 9. Non-polar lipids of other origin can also be added to the oil before the dilution and evaporation processes start.

This will result in emulsions with smaller particles, more even particle size distribution and more reproducible product quality compared to traditional emulsifying methods.

7. APPLICATIONS OF THE INVENTION

We will focus here on certain applications of the unilamellar vesicle dispersions. In release applications of lipophilic additives for use in foods, drugs or cosmetics, the actual component or component mixture in the simplest case is added to the T2 or T7 stem solution before the vesicles are formed via the dilution process, so that actual components become integrated into the bilayer. The different substances that are incorporated in the vesicles are not allowed to effect the lipid phase behavior, and this can be analyzed by phase equilibrium studies. A faster method is to use the strategy outlined in Examples 2-4. Lipophilic additives can also be added to the final dispersion if they spontaneously are solubilized in the lipid bilayer of the vesicles.

Hydrophilic additives can sometimes be solubilized in the water core of the particles if they are added as a solution in the aqueous phase which is used in dilution of the T2 or T7 stem solution into a T3 type of dispersion. The solubilized molecules will then enter the water compartments of the particles, provided that the molecules are small enough. The excess of additive which remains in the outside continuous water phase can then be removed by dialysis.

The different ways to incorporate, encapsulate or solubilize additives for applications mainly in foods and pharmaceuticals will be illustrated by the examples below that are selected so as to illustrate this.

Applications of this invention can be used in the following fields:

7.1. Appetite Regulation

As mentioned in the introduction, one method for appetite regulation has been based on pharmaceutically active substances and documented in clinical trials, involving inhibition of lipase activity in the gastrointestinal tract by liposomal particles. This is now a general accepted therapy against obesity in medical care. The vesicle dispersions according to this invention associate to the lipase present in the intestine. The small size of the vesicles and their long life-time in the intestinal system are important features. This opens a possibility for food products with improved function in appetite regulation.

7.2. Formulation of Drugs for Topical or Gastrointestinal Administration

The incorporation of the drug into the vesicles was described in the introduction to paragraph 4 above. Molecules which are hydrophilic might be added to a pre-prepared dispersion and spontaneously became integrated. The vesicles may incorporate hydrophilic molecules by transient opening/closing processes, for example by ultrasonification and then the drug will then be distributed both inside the vesicles and outside. By dialysis the outside drug molecules can then be removed.

Hydrophobic active molecules are preferably solved together with the starting material of lipids in ethanol used in the water-precipitation/ethanol-evaporation process. Hydrophobic molecules which also are water soluble can be added directly to the final formulation where the molecules will be partitioned between the aqueous and lipid regions.

7.3. A Gastrointestinal Immunomodulating Product

Galactolipids in rose hips have been shown to provide immunomodulating effect and is used for pain relief in joint inflammation conditions (R. Christensen, E. Bartels, R. Altman, A. Astrup, Bliddal, H. Osteoarthritis and Cartilage 16 (2008) 965-972.) It seems likely that our oat lipid galactolipids will have similar effects and have application in therapy for autoimmunological diseases, such as rheumatoid arthritis and multiple sclerosis. A particular advantage might be the particle size and shape, as being one significant factor in recognition by the immune system. About one half of the immune system in humans is located in the gastrointestinal region. We consider the small size of our unilamellar vesicles (in T3) as particularly interesting in order to contribute to the immunological protection achieved by particles and bacteria in the colon environment.

Effects on joint inflammation in rheumatoid arthritis has been linked to the presence of digalactodiglycerides in the rose hip formulations above (Christensen ref rad 12). As our particles has a high content of the same lipid, it should be expected that our dispersions rich in DGDG will have similar effects. Furthermore there have been anecdotal patient reports indicating effects from our oat lipid dispersions on multiple sclerosis.

7.4 Encapsulation of Food Components in the Lipid-Particles for Increased Bioavailability As mentioned above nutrients with low bioavailibility that are incorporated into the dispersed particles according to this invention are expected to have better bioavailibility due to a partition into the lipid aggregates that are absorbed in the GI tract.

Furthermore certain lipophilic food components with a tendency to be oxidized during storage in food products are protected when they are incorporated in the lipid region of liquid-crystalline phases. Lycopen, lutenin and coenzyme Q10 (ubiquinone) are examples where an incorporation into unilamellar vesicles or vesicles of this invention may provide possibilities to manufacture products with increased bioavailability. Hydrophilic compound can be incorporated in the aqueous compartments of the lipid particles in the same way as described in the case of drugs above. Another example of a compound where the bioavailability is very low is curcumin.

8. EXAMPLES

Preparation of a Gel

Example 1 illustrates how the prior art works applied on lipids containing galactolipids.

Example 1

Preparation of an Aqueous Gel of HII-Type

When the T2 fraction is directly diluted with excess of water until the ethanol concentration and the lipid concentration is only a few wt %, see FIG. 5, the liquid-crystalline HII phase is formed which can be unambiguously identified by its birefringent texture. The HII-phase should ultimately be transformed into an L-alpha phase but this transition is extremely slow as mentioned above. Once formed it is impossible to disperse this HII-phase gel. The gel is floating on the top of the solvent. In some cases the gel can be so hard that it is possible to pick the whole gel as a single piece from the solvent using tweezers.

Preparation of Lipid Dispersions

In order to obtain a colloidal dispersion of unilamellar vesicles the following dilution process was developed and used, see Examples 2, 3 and 4 below.

Example 2

Method to Find the Critical Polarity

We started with 5 glass tubes of 5 ml, each filled with 1 ml of PL0126, a fractionated oat oil of type T2. The composition of PL0126 was: 65 lipid % of polar lipids; 25 wt % solvent and the concentration of ethanol in this solvent phase was 55 vol %. This is illustrated as PL0126 in FIG. 6.

Small amounts of five different ethanol/water mixtures were step-wise added up to totally 4 ml in each tube. After each addition of solvent the tubes were shaken by hand for five seconds and then mixed ten seconds using a vortex tub mixer and a droplet was taken for microscopic investigation and the viscosity and phase behaviour was observed.

The concentration of ethanol in the solvent mixtures was 60, 55, 50, 45 and 40 vol %, respectively. These ethanol solutions are denoted as E60, E55, E50, E45 and E40, respectively, in the rest of this document. The compositions in these five tubes were calculated and the results are illustrated as PL0126+E60, PL0126+E55, PL0126+E50, PL0126+E45 and PL+E40, respectively, in FIG. 6. As mentioned in the text for these figures all water and all ethanol data is considered as the average composition of the total mixture. Whether there at certain compositions exists an immiscibility gap between water and ethanol or not is not taken into account. We found this as a practically useful simplification to describe the system. After this dilution the dry solid content became about 15 wt %.

All experiments in this example were performed at room temperature.

After evaluation of the viscosity and phase behaviour in these experiments we could construct the lines "High Viscous", "Dispersion" and "Oil" in FIG. 7.

When evaluating these experiments it is important to note that the rate of particle formation is much higher than the rate of mixing oil and solvent. This means that locally, at the interface between the oil and the solvent, the concentration of the liquid is close to the solvent added. This situation is very important when the viscosity is high in the system.

When the concentration of ethanol in the solvent phase was 55 vol % or higher, an oil phase and a solvent phase occurred. If the sample was allowed to stand for ten minutes or more the oil phase was observed at the bottom of the tube. After an hour or more, a white precipitation of an oil emulsion could be observed above this oil phase. The solvent phase above this precipitation was then opaque. After a long time this solvent phase became crystal clear in most cases. The range where this phase behaviour occurred was below "Oil" and to the right of the line "Dispersion" in FIG. 7.

When the concentration of ethanol in the solvent phase was in the range between 50 and 55 vol %, a solvent-in-oil dispersion occurred. The dispersion was low viscous. The oil phase was the continuous phase. A lot of liposomes occurred in the solvent droplets. The liposomes were in some cases very large, up to 40 µm, see FIG. 4 Based on other experiments we know that the composition of the oil in this "Oil-in-Solvent" part of the dispersion is different compared to T2. The composition of this oil is close to T7, i.e. lower in estolides and lower in triglycerides compared to T2, see Table 1 and WO2010104444

At dilution with E45 the oil was a continuous phase at E55, but partly disintegrated at E50 with droplets in the range 1 to 100 µm, see FIGS. 6, 7 and 3. The range where this phase behaviour occurred was to the left of the line "Dispersion" and to the right of the line "High Viscous" in FIG. 7.

At further dilution with E45 and the concentration of ethanol in the solvent phase was below E50, the solvent phase became the continuous phase and an Oil-in-Solvent dispersion occurred. This dispersion became very fast very high viscous. The solvent phase was very fast filled with very small particles, the majority below 1 µm, the resolution limit for the light microscope. A maximum in viscosity and speed of small particle formation occurred when 4 parts of E45 was added. In that case the dispersion became so thick that after five shakings of the tub in the hand, we could turn the tube upside down and the content stayed in the tube, see FIG. 7

With 4 parts of E50 the mixture remained low viscous. With 4 parts of E40 the mixture became thick, but it lasted 10 minutes before it became that viscous that we could turn it upside down. In this case we could in the microscope detect some particles larger than 1 µm in diameter.

Thus, at ethanol concentrations in the solvent phase below 50 vol %, a high viscous dispersion is formed. This range is to the left of the line named "High Viscous" in FIG. 7.

Based on these experiments we can determine the critical polarity for this oil to be between E50 and E45. The reasons are that:

at E50 the mixture remained low viscous and at E45 the mixture became high viscous. Thus, the viscosity starts to increase rapidly at a higher polarity than E50 but at a lower polarity than E45.

A lot of large liposomes, 1-100 µm, occurred in mixtures between E55 and E50, at E45 all particles was below 1 µm. Thus, the liposome size starts to decrease rapidly at a polarity higher than E50 but at a polarity lower than E45.

A lot of large particles, 1-100 µm, occurred in mixtures between E55 and E50, at E45 all particles was below 1 µm. Thus, the particle size starts to decrease rapidly at a polarity higher than E50 but at a polarity lower than E45. The critical polarity is plotted in FIG. 7.

By using the principles described in this example the critical polarity of any oil can be determined.

Example 3

Illustration of Phase Behaviour at a Dry Solid Concentration Below 12 wt % and at an Ethanol Concentration in the Range 40-55 vol %

A stem solution of type T2, PL0126, was diluted with 9, 19 and 39 parts of E55, respectively. These samples was in turn diluted with pure water, see FIG. 8. The concentrations were calculated as in Example 2. The viscosity and phase behaviour was observed visually and in light microscope.

When the concentration of ethanol in the solvent was above 50 vol % and the dry solid was below 8 wt %, "Free Solvent", "Oil" and "Dispersion" could be observed in the same way as above.

The difference was that the boarder for the "Dispersion" moved slightly towards lower concentrations of ethanol when the dry solid was reduced, see FIG. 9.

Example 4

Production of T3—A Method to Find Suitable Conditions for Adding Water to the Dispersion and a Method to Remove the Ethanol from the Dispersion Stem solutions have been diluted by different ethanol-water solutions, followed by addition of water and evaporation of the ethanol in a rotating lab evaporator. The compositions of the mixtures were calculated in the same way as in Example 2. The particle size was investigated by polarizing light microscope and such samples were taken at different steps in the process.

When the evaporation is performed in a rotating lab evaporator the dry solid can be increased to about 10 wt % and the dispersion remain low viscous all the time. When the dry solid exceed about 10 wt % the dispersion becomes high viscous. The process lines for three examples are illustrated in FIGS. 10-12. The border between the high viscous and the low viscous region can be extended down to zero in ethanol, see FIGS. 10-12.

FIG. 10 T2+27E50

One part, 10 ml, of a stem solution of type T2, PL0126, was diluted step-wise with 27 parts of E50. The dispersion was shaken by hand in an evaporation bottle of 1 liter size. The composition followed the low viscous region and reached the region for "Oil" and "Solvent". The sample was evaporated in a rotating lab evaporator, see FIG. 10.

After completed dilution with E50 the product contained a lot of very small particles, smaller than 1000 nm, but also some larger particles, about 5% of the particles were larger then 1000 nm. At this stage it was not possible to observe any Maltese crosses in the product. With the methods used, it was not possible to detect that any changes in particle size distribution occurred during to the evaporation process.

The dilution was performed at a polarity of the first ethanol-water mixture slightly lower than the critical polarity. In this case no second solvent were used or we can say that the second solvent was the same as the first solvent. The final product after this procedure is called T3.

Samples produced according to this process line were analysed using synchrotron small-angle X-ray scattering analysis. The average particle size was larger than 100 nm.

FIG. 11 T2+9E45

One part, 10 ml, of a stem solution of type T2, PL0126, was diluted step-wise with 9 parts of E45. The dispersion was shaken by hand in an evaporation bottle of 1 liter size. The composition entered and passed the high viscous region and reached the low viscous dispersion region in the end of the dilution. Then 4 parts of water was added and the evaporation started. When 1 part of solvent was evaporated, the dispersion became rather viscous and the evaporation was stopped. One more part of water was added and the evaporation started again. When another part of solvent was evaporated, the dispersion became rather viscous and the evaporation was stopped. One more part of water was added and the evaporation started again. This time the evaporation could continue until the ethanol was below 1 wt % and the dry solid was about 10 wt %, see FIG. 11.

After completed dilution with E45 the product contained a lot of very small particles, smaller than 1000 nm, but also some larger particles, about 1% of the particles were larger then 1000 nm. At this stage it was not possible to observe any Maltese crosses in the product. With the methods used, it was not possible to detect that any changes in particle size distribution occurred during the dilution of the product with water or during the evaporation process.

The dilution was performed at a polarity of the first ethanol-water mixture slightly higher than the critical polarity. The amount of this solvent was so high that the viscosity was reduced in the end of the dilution procedure, see FIG. 11. The second solvent was water. The final product after this procedure is called T3.

FIG. 12 T2+4E45

One part, 10 ml, of a stem solution of type T2, PL0126, was diluted step-wise with 4 parts of E45. The dispersion was shaken by hand in an evaporation bottle of 1 liter size. The composition entered and stayed in the high viscous region. Then 7 parts of water was added and the viscosity was reduced in the end of this dilution procedure. Then the evaporation started. The evaporation continued until the ethanol was below 1 wt % and the dry solid was about 10 wt %, see FIG. 12.

After completed dilution with E45 the product contained a lot of very small particles, smaller than 100 nm. No particles larger then 1000 nm were observed. At this stage it was not possible to observe any Maltese crosses in the product. With the methods used, it was not possible to detect that any changes in particle size distribution occurred during the dilution of the product with water or during the evaporation process.

The dilution was performed at a polarity of the first ethanol-water mixture slightly higher than the critical polarity. The second solvent was water. See FIG. 12. The final product after this procedure is called T3.

Samples produced according to this process line were analysed using synchrotron small-angle X-ray scattering analysis. The average particle size of the vesicles was 40-50 nm.

The Methods from Example 2-4 Applied on Other Oils

Example 5

Production of T4—Preparation of an Aqueous Dispersion of Unilamellar Vesicles Using an Oil of T7-Type as Starting Material After exploration of the high viscous region for the dispersion, in analogy to the description in Examples 2, 3 and 4, we used the following procedure for an oil of T7-type to produce an aqueous dispersion of very small vesicles.

One part, 100 ml, of an oil of type T7, PL13, was mixed with 3.5 parts E42. The dispersion was shaken by hand in an evaporation flask for about 30 seconds. Seven parts of water was added. The dispersion was shaken by hand for about another 30 seconds. The ethanol was removed from the dispersion by evaporation in a vacuum evaporator. This process is illustrated by the process line "PL13+3.5E42" in FIG. 13.

The dilution was performed at a polarity of the first ethanol-water mixture higher than the critical polarity. The second solvent was water. See FIG. 13. The final product after this procedure is called T4.

The final product had a dry solid content of 10 wt %; the content of ethanol was below 0.1 wt % and all the resulting particles were below the detection limit in a light microscope, about 1000 nm, The Effects of Reduced Particle Size and Improved Particle Size Distribution

Example 6

Stability Tests on Different Vesicles, Type T3

To in vitro simulate the conditions in the stomach; we mixed 2 ml of a T3 sample with 2 ml 1M citric acid in a glass tube. This gives a pH of about 3. Then we observed how this mixture behaved over a long time at room temperature.

The initial average particle size was determined using synchrotron small-angle X-ray scattering analysis.

We present results from two process lines. The first sample, T3-1, followed the process line in FIG. 10 and the second sample, T3-2, followed the process line in FIG. 12. The results are summarized in Table 2

The particle size became much smaller using the process-line in FIG. 12, 50 nm, compared to using the process-line in FIG. 10, >100 nm. The sample with the large vesicles, T3-1, was not stable at pH 3. Thus, we do not expect that these vesicles will remain stable while they pass the stomach. The sample with the small vesicles, T3-2, was stable for 10 days at pH 3. Thus, we expect that these small vesicles will remain stable while passing the stomach.

Thus, by diluting an oil containing polar lipids using an ethanol-water solution with a polarity close to critical polarity dispersions with very small particles can be produced. By enter and remain in the high viscous region during the dilution with the first ethanol-water mixture, we could reduce the size of the vesicles, from larger then 100 nm to 50 nm. This difference improved the functional properties of the dispersion to a very high extent.

Example 7

Effects of Oat Oil Vesicles on Satiety

A blinded randomized study with cross-over design was performed on healthy individuals at Lund University hospital and supervised by a clinically experienced MD and PhD. In the study 19 subjects consumed 35 g of lipids in a breakfast meal in the form of an oat lipid dispersion, T3-2 as described in this invention, or in the form of a yoghurt control. Blood samples were analyzed for triacylglycerol, total-, HDL- and LDL-cholesterol, glucose and gastric hormones PYY and GLP-1 before and four times after the meal. These hormones are generally accepted as markers of satiety. Subjective analysis of satiety was measured using a VAS-questionnaire. Participants recorded their food intake before and after the trial.

The satiety hormone PYY was significantly elevated 5 and 7 hrs after and glucose was lower after 5 hrs with oat lipid dispersion compared to control. This coincided with a prolonged elevation of plasma TG concentration. The subjective sensation of satiety and food intake the remaining time of the test day was not significantly different between the groups.

From this study it can be concluded that intake of the oat lipid dispersion induce prolonged intestinal digestion, prolonged chylomicron output accompanied with a PYY increase in healthy individuals. Taken together, the postprandial lipid- and hormone profile after intake of this oat lipid dispersion might induce satiety and reduce overeating.

Other Products Achieved by Dilution Close to the Critical Polarity

Example 8

Preparation of an Oat Oil Free from Ethanol and HII-Particles

An oat oil with a polar lipid concentration of 40 lipid % (HL17) was evaporated in a lab rotavapor to dryness. The ethanol content was below 0.1 wt % in the final product. The process line can be seen in FIG. 14. The product contained a lot of HII particles.

This product has poor emulsifying properties.

Five glass tubes of 5 ml was filled with 1 ml HL17 each. 2 ml of ethanol solutions of E40, E45, E50, E55 and E60 was added to the different glass tubes. The tubes were mixed by hand and for a short vile in a vortex mixer. E40, E45 and E50 became high viscous. The critical polarity became E51.

161 g HL17 was mixed with 320 ml E50 in an evaporator flask. The flask was shaken by hand for 1 min and evaporated to dryness in a rotavapor. The ethanol content was below 0.1% in the final product. The process line can be seen in FIG. 14. The product did not contain any HII particles.

By using the ethanol-water dilution/evaporation method we have managed to circumvent the range where HII-particles are formed.

The oil produced in this way is called T9.

This oil has very good emulsifying properties.

To a test tube which is half-filled with distilled water, we carefully add T9 on the surface in an amount of 10% (w/w) calculated on the amount of water. The floating oil film is within an hour swollen in the water contact zone towards a drop-shape down into the water, but still it remains homogeneous and transparent. Then during the next 15-25 hours (with kinetics related to amounts and interface geometry) without shaking or any mechanical force applied, a homogeneous dispersion is obtained. This can be regarded as a spontaneous emulsification process driven by reduction of interfacial tension.

26 g of SFO10 was mixed with 52 ml E45. This mixture was shaken by hand in an evaporation flask for 1 min. 52 ml of water was added and the flask was shaken 1 min by hand. The ethanol was evaporated to a dry solid of 42% and the ethanol concentration to below 0.1 wt %, see FIG. 15. The emulsion looked like a mayonnaise and all particles were below 1 μm in diameter.

TABLE 1

Composition of some oils used as stem solutions

| | | solvent | | Composition | | | | | |
|---|---|---|---|---|---|---|---|---|---|
| | | | | | | Lipids | | | |
| | | | | | | | | | Estolides/ |
| Fraction | | EtOH | Water | dry solid | NL[1] | PL[2] | Sugar[3] | GL/PhL[4] | DGDG[5] |
| name | preparation method | solvent % | | wt % | lipid % | lipid % | lipid % | ratio | ratio |
| T2[6] | Heavy Polar Lipids[6] | 60 | 40 | 75 | 35 | 65 | 4 | 1.0 | 1.0 |
| T7[6] | Low in Estolides[6] | 60 | 40 | 75 | 15 | 85 | 9 | 1.0 | 0.3 |
| HL17[7] | T1[6] + T2[6] | 61 | 39 | 80 | 60 | 40 | 5 | 1.0 | 1.0 |
| SFO10 | SFO[8] + T2[6] | 55 | 45 | 96 | 90 | 10 | 0 | 1.0 | 1.0 |

[1] NL  Lipids with non-polar functionality  more than 90% triglycerides
[2] PL  Lipids with polar functionality  Galactolipids and Phospholipids
[3] Sugar    more than 90% saccaros
[4] GL  Galactolipids  DGDG more than 70% of GL
 PhL  Phospholipids  PC + PE about 50% of PhL
   This ratio is 1.0 in crude oat oil
[5] Estolides  DGDG with at least one fatty acid containing an esterified OH group
 DGDG  di-galatosyl-di-acyl-glyceride
   This ratio is 1.0 in crude oat oil
[6] Oat oil fraction from fractionation procedures using ethanol, water and sugar, described in WO2010104444
[7] HL17  Oat oil fraction of T2-type
[8] SFO  Sunflower oil

Example 9

Oil-in-Water Emulsion Prepared Using the Ethanol-Water Dilution/Evaporation Process Sunflower oil and oat oil of type T2, PL090219, were mixed to two different concentrations of polar lipids, 10 and 2 lipid %. The critical polarity was determined by mixing, 1 ml of oil and 1 ml of different ethanol mixtures (E0, E35, E40, E45, E50, E55, E60), in glass tubes of 5 ml and shake the tubes by hand and by a vortex mixer. The viscosity of the samples was observed visually and by shaking. The particle size was observed in microscope with polarized light and phase contrast.

The oil with 2 lipid % polar lipids gave all a low viscous emulsion. The samples mixed with E45 and E50 gave the smallest particles, 0.5-5 um. This indicated a critical polarity of E52. However, the amount of polar lipids seems to be too low to give a good emulsion.

The oil with 10 lipid % polar lipids, SFO10, gave high viscous emulsion at E35, E40 and E45. The sample with E45 gave the smallest particles, all particles below 1 um. This gave a critical polarity of E47.

TABLE 2

Properties of vesicles from different processes

| Sample | | particle size[1] average | dry solid | stability[2] | |
|---|---|---|---|---|---|
| | | | | pH = 3 | pH = 7 |
| name | process | nm | wt % | time | time |
| T3-1 | 27E50 + water[3] | >100 | 10 | <1 min | >12 month |
| T3-2 | 4E45 + water[4] | 50 | 10 | 10 days | >12 month |

[1] Determined with synchrotron small-angle X-ray scattering analysis
[2] time before visible changes occured
[3] see process in FIG. 10 see process in FIG. 12

The invention claimed is:

1. A method for preparing an aqueous colloidal dispersion of polar lipids in an ethanol-water mixture, comprising:
   (i) diluting an oil containing polar and non-polar lipids with an ethanol-water mixture, said mixture having an ethanol concentration, calculated as volume % based on the total amount of ethanol and water, in the range of from 15 volume % units below the critical polarity of the ethanol-water mixture with respect to said oil to 15 volume % units above said critical polarity,
   wherein the critical polarity of said ethanol-water mixture is in the range of 25-75 volume % ethanol in the water-ethanol-mixture, and
   wherein said polar lipids comprise galactolipids and are of a type that will form a hexagonal HII-phase at direct water exposure; and (ii) upon said dilution with the ethanol-water mixture, forming a lamellar liquid-crystalline phase in the form of liposomes, without first forming a hexagonal HII-phase, wherein the liposomes comprise at least 50 lipid % of polar lipids and at least 2 lipid % of non-polar lipids, the lipid % being the weight % based on the total amount of lipids.

2. The method as claimed in claim 1, wherein said ethanol-water mixture has an ethanol concentration calculated as volume % based on the total amount of ethanol and water, in the range of from 10 volume % units below the critical polarity of the ethanol-water mixture with respect to said oil, to 10 volume % units above said critical polarity.

3. The method as claimed in claim 1, wherein the critical polarity of said ethanol-water mixture is in the range of 30-70 volume % ethanol in the water-ethanol mixture.

4. The method as claimed in claim 1, wherein the (i) diluting step further comprises, after diluting the oil in a first ethanol-water mixture thereby forming a dispersion, diluting said dispersion in a second ethanol-water mixture and/or with water, wherein said polar lipids form colloidal particles in the form of liposomes, cubic particles and/or oil droplets coated by lamellar liquid-crystalline phase.

5. The method as claimed in claim 4, wherein the second ethanol-water mixture contains a higher proportion of water than the first ethanol-water mixture.

6. The method as claimed in claim 1, further comprising obtaining a colloidal dispersion of said liposomes.

7. The method as claimed in claim 6, wherein said liposomes are in the form of unilamellar vesicles having one bilayer of polar lipids.

8. The method as claimed in claim 1, wherein said oil contains at least 25 weight % monoglycerides of oleic and/or linolic acid as calculated on the total amount of lipids in said oil thereby forming a colloidal dispersion of cubosomes.

9. The method as claimed in claim 1, further comprising evaporating ethanol from the dispersion to provide an aqueous dispersion containing less than 10 weight % ethanol.

10. The method as claimed in claim 1, wherein said polar lipids also comprise phospholipids.

11. The method as claimed in claim 1, wherein said oil contains between 30-95 lipid % non-polar lipids, and said dispersion contains at least 30 weight % total lipids, resulting in an oil-in-water emulsion in which the non-polar lipids form oil droplets that are coated by the lamellar liquid-crystalline phase of said polar lipids.

12. The method as claimed in claim 1, further comprising evaporating ethanol and water from said dispersion to provide an oil containing less than 1 wt % ethanol.

13. The method as claimed in claim 1, wherein said oil is derived from oat.

14. An aqueous colloidal dispersion of lipids, the dispersion obtainable by the following method:
(i) diluting an oil comprising polar and non-polar lipids with an ethanol-water mixture, said mixture having an ethanol concentration, calculated as volume % based on the total amount of ethanol and water, in the range of from 15 volume % units below the critical polarity of the ethanol-water mixture with respect to said oil to 15 volume % units above said critical polarity,
wherein the critical polarity of said ethanol-water mixture is in the range of 25-75 volume % ethanol in the water-ethanol-mixture, and
wherein said polar lipids comprise galactolipids and are of a type that will form a hexagonal HII-phase at direct water exposure; and
(ii) upon said dilution with the ethanol-water mixture, forming a lamellar liquid-crystalline phase in the form of liposomes, without first forming a hexagonal HII-phase,
wherein the liposomes comprise at least 50 lipid % of polar lipids, and at least 2 lipid % of non-polar lipids, the lipid % being the weight % based on the total amount of lipids.

15. The dispersion as defined in claim 14, wherein the liposomes have a mean diameter of less than 100 nm.

16. The dispersion as defined in claim 14, wherein at least 80% of the liposomes have a diameter of less than 200 nm.

17. The dispersion as defined in claim 14, wherein the liposomes have a mean diameter of not more than 80 nm.

18. The dispersion as defined in claim 14, wherein at least 80% of the liposomes have a diameter of less than 100 nm.

19. The dispersion as defined in claim 14, wherein the liposomes have a mean diameter in the range of 30-60 nm.

20. The dispersion as defined in claim 14, wherein the liposomes are unilamellar vesicles having one bilayer of polar lipids.

21. An aqueous colloidal dispersion of polar lipids and non-polar lipids,
wherein at least 25 weight % of said polar lipids are monoglycerides of oleic and/or linolic acid as calculated on the total amount of lipids, said polar lipids comprising galactolipids, and
wherein the polar lipids are in the form of colloidal cubosomes.

22. The dispersion as defined in claim 14, wherein the polar lipids are derived from plants, animals or microbiological species.

23. The dispersion as defined in claim 22, wherein the polar lipids are derived from cereal grains or leaves.

24. The dispersion as defined in claim 23, wherein the polar lipids are derived from oat.

25. The dispersion as defined in claim 14, wherein the polar lipids further comprise phospholipids.

26. The dispersion as defined in claim 14, wherein the dispersion has a dry solid content of less than 20 weight %.

27. An aqueous dispersion in the form of an oil-in-water emulsion of polar lipids comprising galactolipids and non-polar lipids,
wherein the non-polar lipids form oil droplets that are coated by a lamellar liquid-crystalline phase of said polar lipids, and
wherein said polar lipids comprising galactolipids are of a type that will form a hexagonal HII-phase at direct water exposure.

28. A pharmaceutical formulation, comprising the aqueous colloidal dispersion as defined claim 14, and optionally a pharmaceutically acceptable adjuvant, diluent or carrier.

29. The pharmaceutical formulation according to claim 28, wherein the dispersion is an active ingredient.

30. The pharmaceutical formulation according to claim 28, wherein the dispersion is a carrier for release of an active ingredient.

31. A cosmetic composition, comprising the aqueous colloidal dispersion as defined in claim 14.

32. A food composition or food supplement composition, comprising the aqueous colloidal dispersion as defined in claim 14.

33. The food composition or food supplement composition as defined in claim 32, wherein said food composition or food supplement composition is margarine, oil, cream, milk, yoghurt, cheese, flour, juice, shot or soft drink.

34. An animal feed composition, comprising the aqueous colloidal dispersion as defined in claim 14.

35. An article, comprising the aqueous colloidal dispersion as defined in claim 14.

36. The dispersion as defined in claim 14, wherein the liposomes comprise at least 60 lipid % of polar lipids, and a remainder lipid % of non-polar lipids.

37. The dispersion as defined in claim 14, wherein the liposomes comprise at least 75 lipid % of polar lipids, and a remainder lipid % of non-polar lipids.

38. The dispersion as defined in claim 14, wherein the liposomes comprise at least 5 lipid % of non-polar lipids.

39. The dispersion as defined in claim 14, wherein the liposomes comprise at least 10 lipid % of non-polar lipids.

40. The dispersion as defined in claim 14, wherein the liposomes comprise 15-35 lipid % of non-polar lipids.

41. The pharmaceutical formulation according to claim 28, for treating obesity, reducing blood lipid levels, diabetes type II and/or autoimmune diseases.

\* \* \* \* \*